US006627795B1

(12) United States Patent
Coughlan et al.

(10) Patent No.: US 6,627,795 B1
(45) Date of Patent: Sep. 30, 2003

(54) CAROTENOID BIOSYNTHESIS ENZYMES

(75) Inventors: Sean J. Coughlan, Hockessin, DE (US); Mark E. Williams, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 192 days.

(21) Appl. No.: 09/691,270

(22) Filed: Oct. 18, 2000

Related U.S. Application Data

(63) Continuation of application No. PCT/US99/08789, filed on Apr. 22, 1999.
(60) Provisional application No. 60/083,042, filed on Apr. 24, 1998.

(51) Int. Cl.[7] .......................... A01H 3/00; A61K 38/43; C07H 21/04; C07K 14/415; C12N 5/14

(52) U.S. Cl. .......................... 800/278; 435/6; 435/69.1; 435/183; 435/410; 435/419; 435/252.3; 435/320.1; 530/350; 530/370; 536/23.2; 536/23.6; 536/24.1; 800/295

(58) Field of Search .......................... 435/6, 69.1, 183, 435/410, 419, 252.3, 320.1; 530/370, 350; 536/23.2, 23.6, 24.1; 800/278, 295

(56) References Cited

U.S. PATENT DOCUMENTS 5,705,624 A    1/1998   Fitzmaurice et al.

FOREIGN PATENT DOCUMENTS

| WO | 96/02650 A2 | 2/1996 |
| WO | 96/38566 | 12/1996 |
| WO | 97/46690 | 12/1997 |

OTHER PUBLICATIONS

EMBL Sequence Library Accession No: C74590, Sep. 21, 1997, Yamamoto, K. et al., Rice cDNa from Panicle (between 3 cm to 10 cm).
EMBL Sequence Library Accession No: C73801, Sep. 20, 1997, Yamamoto, K. et al., Rice cDNa from Panicle (longer than 10cm).
Derwent Publications LITD., AN–1998–264853, Iwate Ken, XP–002129005.
Swissprot Sequence Library Accession No: 022375, Jan. 01, 1998, Castrignano, F. et al., XP–002129000.
EMBL Sequence Library Accession No: AA051885, Sep. 11, 1996, Baysdorfer, C., The Maize cDNa Program, XP–002129006.
Anne Frey et al., Plant Molecular Biology, vol. 39:1267–1274, 1999, Engineering Seed Dormancy by the Modification of Zeaxanthin Epoxidase Gene Expression.
EMBL Sequence Library Accession No: AF071888, Jun. 29, 1998, Mbequie–A–Mbeguie, D. et al., Molecular Cloning and Nucleotide Sequence of a Zeaxanthin Epoxicase from apricot Fruit.
Peter K. Burkhardt et al., The Plant Journal, vol. 11(5):1071–1078, 1997, Transgenic Rice (*Oryza sativa*) endosperm Expressing Daffodil (*Narcissus pseudonarcissus*) Phytoene Synthase Accumulates Phytoene, a Key Intermediate of Provitamin A Biosynthesis.
Gerhard Sandmann et al., Zeitschrift Fur Naturforschung, vol. 51(7–8):534–538, 07–1996, A New Non–Radioactive Assay of Phytoene Desaturase to Evaluate Bleaching Herbicides.

(List continued on next page.)

Primary Examiner—Phuong T. Bui

(57) ABSTRACT

This invention relates to an isolated nucleic acid fragment encoding a carotenoid biosynthetic enzyme. The invention also relates to the construction of a chimeric gene encoding all or a portion of the carotenoid biosynthetic enzyme, in sense or antisense orientation, wherein expression of the chimeric gene results in production of altered levels of the carotenoid biosynthetic enzyme in a transformed host cell.

14 Claims, 2 Drawing Sheets

```
SEQ ID NO:27  DPDIVLPGN---------------------------------------------
SEQ ID NO:28  MAIILVRAASPGL--SAADSISHQ-GTLQCSTLLKTKRPAARRWMPCSLLGLHPWEAGRP
SEQ ID NO:02  EREEEERVLGWGLLGDAYDRCGEVCAEYAKTFYLGTQLMTPERRKAVW--AIYVW-CRRT
SEQ ID NO:14  MSGVLLWVSC-----GPKENINSL-VSFSCRSSSGGER-TQKRFSGISFAS---------
              1                                                          60

SEQ ID NO:27  ---------------------------------------------
SEQ ID NO:28  SPAVYSSLFVNPAGEAVVSSEQKVYDVVLKQA-ALLKRQLRTPVLD---ARPQDMDMP--
SEQ ID NO:02  DELVDGPNASYITPTALDRWEKRLEDLFEGRPYDMYDAALSDTVSKFPVDIQPFKDMVQG
SEQ ID NO:14  GTSAFSS--AVAATETSRSSEERVYEVVLKQA-ALVKEHKRGTKIALDLDKDVEADFN--
              61                                                         120

*   *    *     *      *  **  ***   **  *  *******************
SEQ ID NO:27  --LGLLSEAYDRCGEVCAEYAKTFYL-GTMLMTPDRRRAIWAIYVWCRRTDELVDGPNAS
SEQ ID NO:28  -RNGL-KEAYDRCGEICEEYAKTFYL-GTMLMTEERRRAIWAIYVWCRRTDELVDGPNAN
SEQ ID NO:02  MRLDLWKSRYMTFDEL---YLYCYVVAGTQLMTPERRKAVWAIYVWCRRTDELVDGPNAS
SEQ ID NO:14  -NVDLLNAAYDRCGEVCAEYAKTFYL-GTQLMTAERRKAIWAIYVWCRRTDELVDGPNAS
              121                                                        180

**  ******  **   *   ***  **  *****   *    *  *****  **    ***  **  *  **
SEQ ID NO:27  HITPQALDRWEARLEDIFNGRPFDMLDAALSDTVSRFPVDIQPFRDMVEGMRMDLWKSRY
SEQ ID NO:28  YITPTALDRWEKRLEDLFTGRPYDMLDAALSDTISRFPIDIQPFRDMIEGMRSDLRKTRY
SEQ ID NO:02  YITPTALDRWEKRLEDLFEGRPYDMYDAALSDTVSKFPVDIQPFKDMVQGMRLDLWKSRY
SEQ ID NO:14  HITPGALDRWEQRLSDVFEGRPYDMYDAALSHTVSKYPVDIQPFKDMIEGMRVDLRKSRY
              181                                                        240
```

OTHER PUBLICATIONS

Manuela Albrecht et al., European J. Biochem., vol. 236:115–120, 1996, Biochemical Characterization of Purified Beta–Carotene Desaturase from Anabaena PCC 7120 after Expression in *Escherichia coli* .

Glenn E. Bartley et al., Plant Cell, vol. 7:1027–1038, Jul. 1995, Plant Carotenoids: Pigments for Photoprotection, Visual Attraction, and Human Health.

Glenn E. Bartley et al., Journ. of Biol. Chem., vol. 268(34):25718–25721, Dec. 5, 1993, cDNA Cloning, Expression during Development, and Genome Mapping of PSY2, a Second Tomato Gene Encoding Phytoene Synthase.

Brent Buckner et al., Genetics, vol. 143:479–488, May 1996, The y1 Gene of Maize Codes for Phytoene Synthase.

Corinne Audran et al., Plant Phys., vol. 118:1021–1028, 1998, Expression Studies of the Zeaxanthin Epoxidase Gene in *Nicotiana plumbaginifolia*.

Larem Bicj et a:/. FEBS :etters. vol.:376:45–48, 1995, FAD is a further essential cofactor of the NAD(P)H and O2–dependent Zeaxanthin–Epoxidase.

M. L. Scott et al., Poultry Science, vol. 47:863–872, 1968, Studies of Egg Yolk Pigmentation.

National Center For Biotechnology Information General Identifier No. 1098664, Aug. 30, 1996, Buckner, B. et al., The y1 Gene of Miaze Codes for Phytoene Synthase.

National Center For Biotechnology Information General Identifier No. 413731, May 26, 1994, Bartley, G. E et al., Nucleotide Sequence of an Arabidopsis cDNA for Phytoene Synthase.

Pablo A. Scolnik et al., Plant Phys. vol. 104:1471–1472, 1994, Nucleotide Sequence of an Arabidopsis cDNA for Phytoene Synthase.

National Center For Biotechnology Information General Identifier No. 437019, Jan. 4, 1994, Bartley, G.E. et al., cDNA Cloning, Expression during Development, and Genome Mapping of PSY2, a Second Tomato Gene Encoding Phytoene Synthase.

National Center For Biotechnology Information General Identifier No. 870984, Jun. 13, 1995, Karvouni, Z. et al., Isolation and Characterisation of a melon cDNA Clone Encoding Phytoene Synthase.

Zoi Karvouini, Plant Mol. Biol., vol. 27:1153–1162, 1995, Isolation and Characterisation of a Melon cDNA Clone Encoding Phytoene Synthase.

National Center For Biotechnology Information General Identifier No. 433993, Feb. 5, 1994, Kuntz, M.

S. Romer et al., Biochem. Biophys. Res. Comm., vol. 196(3):1414–1421, Nov. 15, 1993, Expression of the Genes Encoding the Early Carotenoid Biosynthetic Enzymes in Capsicum Annum.

National Center For Biotechnology Information General Identifier No. 585749, Feb. 1, 1996, Romer, S. et al., Expression of the Genes Encoding the Early Carotenoid Biosynthetic Enzymes in Capsicum Annum.

National Center For Biotechnology Information General Identifier No. 1346883, Oct. 1, 1996, Buckner, B. et al., The y1 Gene of Maize Codes for Phytoene Synthase.

National Center For Biotechnology Information General Identifier No. 585747, Feb. 1, 1996, Bartley, G.E. et al., cDNA Cloning, Expression during Development, and Genome Mapping of PSY2, a Second Tomato Gene Encoding Phytoene Synthase.

National Center For Biotechnology Information General Identifier No. 1709885, Jul. 15, 1998, Schledz, M. et al., Nucleotide Sequence of a Narcissus Pseudonarcissus cDNA for Phytoene Synthase.

National Center For Biotechnology Information General Identifier No. 1346882, Feb. 1, 1996, Karvouni, Z. et al., Isolation and Characterisation of a Melon cDNA Clone Encoding Phytoene Synthase.

National Center For Biotechnology Information General Identifier No. 1098665, Aug. 30, 1996, Buckner, B. et al., The y1 Gene of Maize Codes for Phytoene Synthase.

National Center For Biotechnology Information General Identifier No. 1772984, Oct. 27, 1997, Burbidge, A. et al., Strcuture and Expression of a cDNA Encoding Zeaxanthin Epoxidase, Isolated from a Wilt–Related Tomato (*Lycopersicon esculentum* Mill.).

Alan Burbidge et al., Journ. of Exp. bot., vol. 48(314):1749–1750, Sep. 1997, Strcuture and Expression of a cDNA Encoding Zeaxanthin Epoxidase, Isolated from a Wilt–Related Tomato (*Lycopersicon esculentum* Mill.).

National Center For Biotechnology Information General IdentifierNo. 1370273, Jun. 4, 1996, Marin, E. et al., Molecular Idenfitication of Zeaxanthin Epoxidase of Nicotiana Plumbaginifolia, a Gene Involved in Abscisic Acid Biosynthesis and Corresponding to the ABA Locus of *Arabidopsis thaliana*.

Elena Marin et al., Embo J., vol. 15(10):2331–2342, 1996, Molecular Identification of Zeaxantin Epoxidase of Nicotiana Plumbaginifolia, a Gene Involved in Abscisic Acid Biosynthesis and Corresponding to the ABA Locus of *Arabidopsis thaliana*.

National Center For Biotechnology Information General Identifier No. 3264757, Feb. 4, 2000, Mbeguie–A–Mbeguie, D. et al., Molecular Cloning and Nucleotide Sequences of PA–ZE and PA–ZE2, two cDNAs from Apricot Fruit Coding for a Zeaxanthin Epoxidase. Gene Expression During Fruit Ripening.

Mbequie–A–Mbeguie, D. et al., Plant Phys., vol. 122:291–293, 1/00, Molecular Cloning and Nucleotide Sequences of PA–ZE and PA–ZE2, two cDNAs from Apricot Fruit Coding for a Zeaxanthin Epoxidase. Gene Expression During Fruit Ripening.

Ute Neudert et al., Biochimica et Biophysica Acta, vol. 1392:51–58, 1998, Expression of an Active Phytoene Synthase from Erwinia Uredovora and Biochemical Properties of the Enzyme.

Florence Bouvier et al., Journ. of Biol. Chem., vol. 271(46):28861–28867, Nov. 15, 1996, Cloning, Expression, Functional Reconstitution, and Regulation of beta–Cyclohexenyl Carotenoid Epoxidase from Pepper (*Capsicum annum*).

FIGURE 1A

```
SEQ ID NO:27                                                     DPDIVLPGN-----------------------------------------
SEQ ID NO:28   MAIILVRAASPGL--SAADSISHQ-GTLQCSTLLKTKRPAARRWMPCSLLGLHPWEAGRP
SEQ ID NO:02   EEEEEERVLGWGLLGDAYDRCGEVCAEYAKTFYLGTQLMTPERRKAVW--AIYVW-CRRT
SEQ ID NO:14   MSGVLLWVSC------GPKENINSL-VSFSCRSSSGGER-TQKRFSGISFAS--------
                1                                                          60

SEQ ID NO:27   ----------------------------------------------------
SEQ ID NO:28   SPAVYSSLPVNPAGEAVVSSEQKVYDVVLKQA-ALLKRQLRTPVLD---ARPQDMDP--
SEQ ID NO:02   DELVDGPNASYITPTALDRWEKRLEDLFEGRPYDMYDAALSDTVSKFPVDIQPFKDMVQG
SEQ ID NO:14   GTSAFSS--AVAATETSRSSEERVYEVVLKQA-ALVKEHKRGTKIALDLDKDVEADFN--
                61                                                         120

*    ******** **   **    * *  *** ** ********************
SEQ ID NO:27   --LGLLSEAYDRCGEVCAEYAKTFYL-GTMLMTPDRRRAIWAIYVWCRRTDELVDGPNAS
SEQ ID NO:28   -RNGL-KEAYDRCGEICEEYAKTFYL-GTMLMTEERRRAIWAIYVWCRRTDELVDGPNAN
SEQ ID NO:02   MRLDLWKSRYMTFDEL---YLYCYYVAGTQLMTPERRKAVWAIYVWCRRTDELVDGPNAS
SEQ ID NO:14   -NVDLLNAAYDRCGEVCAEYAKTFYL-GTQLMTAERRKAIWAIYVWCRRTDELVDGPNAS
                121                                                        180

** ******* **   ** **   *  *** **   *** ***********
SEQ ID NO:27   HITPQALDRWEARLEDIFNGRPFDMLDAALSDTVSRFPVDIQPFRDMVEGMRMDLWKSRY
SEQ ID NO:28   YITPTALDRMEKRLEDLFTGRPYDMLDAALSDTISRFPIDIQPFRDMLEGMRSDLRKTRY
SEQ ID NO:02   YITPTALDRWEKRLEDLFEGRPYDMYDAALSDTVSKFPVDIQPFKDMVQGMRLDLWKSRY
SEQ ID NO:14   HITPGALDRWEQRLSDVFEGRPYDMYDAALSHTVSKYPVDIQPFKDMIEGMRVDLRKSRY
                181                                                        240
```

FIGURE 1B

```
             ***** * *********** ** **** * **** *  **  *  ********************
SEQ ID NO:27 NNFDELYLYLCYYVAGTVGLMSVPIMGIAPESKATTESVYNAALALGIANQLTNILRDVGE
SEQ ID NO:28 NNFDELYMYCYYVAGTVGLMSVPVMGIATESKATTESVYSAALALGIANQLTNILRDVGE
SEQ ID NO:02 MTFDELYLYLCYYVAGTVGLMTVPVMGIAPDSKASTESVYNAALALGIANQLTNILRDVGE
SEQ ID NO:14 NNFDELYLYLCYYVAGTVGLMSVPVMGIAPESNASSESIYNAALALGIANQLTNILRDVGE
                                                                      300
             241

****** *** ********* ***  *** **  ***  ** *** ** *** ** **
SEQ ID NO:27 DARRGRVYLPQDELAQAGLSDEDIFAGKVTDKWRIFMKKQIQRARKFFDEAEKGVTELSS
SEQ ID NO:28 DARRGRIYLPQDELAQAGLSDEDIFKGVVTNRWRNFMKRQIKRARMFFEEAERGVNELSQ
SEQ ID NO:02 DARRGRIYLPLDELAQAGLTEEDIFRGKVTGKWRRFMKGQIQRARLFFDEAEKGVTHLDS
SEQ ID NO:14 DARRGRVYLPQDELAQAGLSDDDIFRGRVTDKWRKFMKGQIKRARMFFDEAERGVAELNS
                                                                      360
             301

******* *** * ****  ***  *********** ***  * **** ** ** **
SEQ ID NO:27 ASRMPVLASLLLYRKILDEIEANDYNNFTRRAYVSKPKKLLTLPIAYARSLVPPKSTSCP
SEQ ID NO:28 ASRMPVWASLLLYRQILDEIEANDYNNFTKRAYVGKGKKLLALPVAYGKSLLLP----CS
SEQ ID NO:02 ASRWPVLASLMLYRQILDAIEANDYNNFTKRAYVGKAKKLLSLPLAYARAAVAP.-----
SEQ ID NO:14 ASRMPVWASLLLYRQILDSIEANDYNNFTKRAYVGKVKKLLSLPTAYGFSLLGPQKFTKM
                                                                      420
             361

SEQ ID NO:27 L--AKT
SEQ ID NO:28 LRNGQT
SEQ ID NO:02 ------
SEQ ID NO:14 VR--R.
             421 426
```

CAROTENOID BIOSYNTHESIS ENZYMES

CROSS-REFERENCE TO RELATED APPLICATION

This application is a continuation of Application No. PCT/US99/08789 filed Apr. 22, 1999, which claims priority benefit of U.S. Provisional Application No. 60/083,042, filed Apr. 24, 1998.

FIELD OF THE INVENTION

This invention is in the field of plant molecular biology. More specifically, this invention pertains to nucleic acid fragments encoding enzymes of the carotenoid biosynthesis pathway in plants and seeds.

BACKGROUND OF THE INVENTION

Plant carotenoids are orange and red lipid-soluble pigments found embedded in the membranes of chloroplasts and chromoplasts. In leaves and immature fruits the color is masked by chlorophyll but in later stages of development these pigments contribute to the bright color of flowers and fruits. Carotenoids protect against photoxidation processes and harvest light for photosynthesis. The carotenoid biosynthesis pathway leads to the production of abscisic acid with intermediaries useful in the agricultural and food industries as well as products thought to be involved in cancer prevention. (Bartley, G. E., and Scolnik, P. A. (1995) *Plant Cell* 7:1027–1038).

Phytoene synthase carries out the first step in the carotenoid biosynthetic pathway converting geranylgeranyl diphosphate to phytoene. There are two different phytoene synthases in tomato with different expression patterns: one is expressed at higher levels in mature fruits while the other one is expressed at higher levels in leaves (Bartley, G. E., Scolnik, P. A. (1993) *J. Biol Chem.* 268:25718–25721). It has been speculated that in corn at least two different alleles of phytoene synthase should be present but only one has been identified to date (Buckner, B. et al. (1996) *Genetics* 143:479–488).

In the next step of the carotenoid biosynthesis pathway, phytoene desaturase transforms phytoene into phytofluene. After another desaturation step, the enzyme zeta-carotene desaturase (carotene 7, 8 desaturase; EC 1.134.99.30) converts the lightly colored zeta-carotene to neurosporene which is further desaturated into lycopene. Lycopene may have one of two different fates: through the action of lycopene epsilon cyclase it may become alpha carotene, or it may be transformed into beta carotene by lycopene cyclase. Beta-carotene dehydroxylase converts beta-carotene into zeaxanthin. Zeaxanthin epoxidase transforms zeaxanthin into violxanthin and eventually abscisic acid. The genes encoding this chloroplast-imported protein have been identified in *N. plumbaginifolia*, pepper and tomato. Zeaxanthin epoxidase appears to also be involved in protection from environmental stress (Corinne A. et al. (1998) *Plant Phys.* 118:1021–1028) and uses FAD as a cofactor (Buch, K. et al. (1995) *FEBS Lett.* 376:45–48).

Zeaxanthin is the bright orange product highly prized as a pigmenting agent for animal feed which makes the meat fat, skin, and egg yolks a dark yellow (Scott, M. L. et al. (1968) *Poultry Sci.* 47:863–872). Gram per gram, zeaxanthin is one of the best pigmenting compounds because it is highly absorbable. Yellow corn, which produces one of the best ratios of lutein to zeaxanthin contains in average 20 to 25 mg of xanthophyll per kg while marigold petals yield 6,000 to 10,000 mg/kg.

SUMMARY OF THE INVENTION

The instant invention relates to isolated nucleic acid fragments encoding carotenoid biosynthetic enzymes. Specifically, this invention concerns an isolated nucleic acid fragment encoding a phytoene synthase or a zeaxanthin epoxidase. In addition, this invention relates to a nucleic acid fragment that is complementary to the nucleic acid fragment encoding phytoene synthase or zeaxanthin epoxidase.

An additional embodiment of the instant invention pertains to a polypeptide encoding all or a substantial portion of a carotenoid biosynthetic enzyme selected from the group consisting of phytoene synthase and zeaxanthin epoxidase.

In another embodiment, the instant invention relates to a chimeric gene encoding a phytoene synthase or a zeaxanthin epoxidase, or to a chimeric gene that comprises a nucleic acid fragment that is complementary to a nucleic acid fragment encoding a phytoene synthase or a zeaxanthin epoxidase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a phytoene synthase or a zeaxanthin epoxidase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a phytoene synthase or a zeaxanthin epoxidase in a transformed host cell comprising: a) transforming a host cell with a chimeric gene comprising a nucleic acid fragment encoding a phytoene synthase or a zeaxanthin epoxidase; and b) growing the transformed host cell under conditions that are suitable for expression of the chimeric gene wherein expression of the chimeric gene results in production of altered levels of phytoene synthase or zeaxanthin epoxidase in the transformed host cell.

An addition embodiment of the instant invention concerns a method for obtaining a nucleic acid fragment encoding all or a substantial portion of an amino acid sequence encoding a phytoene synthase or a zeaxanthin epoxidase.

A further embodiment of the instant invention is a method for evaluating at least one compound for its ability to inhibit the activity of a phytoene synthase or a zeaxanthin epoxidase, the method comprising the steps of: (a) transforming a host cell with a chimeric gene comprising a nucleic acid fragment encoding a phytoene synthase or a zeaxanthin epoxidase, operably linked to suitable regulatory sequences; (b) growing the transformed host cell under conditions that are suitable for expression of the chimeric gene wherein expression of the chimeric gene results in production of phytoene synthase or zeaxanthin epoxidase in the transformed host cell; (c) optionally purifying the phytoene synthase or the zeaxanthin epoxidase expressed by the transformed host cell; (d) treating the phytoene synthase or the zeaxanthin epoxidase with a compound to be tested; and (e) comparing the activity of the phytoene synthase or the zeaxanthin epoxidase that has been treated with a test compound to the activity of an untreated phytoene synthase or zeaxanthin epoxidase, thereby selecting compounds with potential for inhibitory activity.

BRIEF DESCRIPTION OF THE DRAWING AND SEQUENCE DESCRIPTIONS

The invention can be more fully understood from the following detailed description and the accompanying drawing and Sequence Listing which form a part of this application.

FIG. 1 depicts the amino acid sequence alignment between the phytoene synthase from corn contig assembled of clones csi1.pk0034.d8 and p0008.cb31d95rb (SEQ ID NO:2), soybean clone sl2.pk0045.b10 (SEQ ID NO:14), *Lycopersicon esculentum* (NCBI gi Accession No. 585747, SEQ ID NO:27) and *Zea mays* (NCBI gi Accession No. 1346883, SEQ ID NO:28). Amino acids which are conserved among all sequences are indicated with an asterisk (*). Dashes are used by the program to maximize alignment of the sequences.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the contig assembled from the entire cDNA insert in clone csi1.pk0034.d8 and a portion of the cDNA insert in clone p0008.cb31d95rb encoding an entire corn phytoene synthase 2.

SEQ ID NO:2 is the deduced amino acid sequence of an entire corn phytoene synthase 2 derived from the nucleotide sequence of SEQ ID NO:1.

SEQ ID NO:3 is the nucleotide sequence comprising the contig assembled from a portion of the cDNA insert in clones p0121.cfrmo87r, p0091.cmarc67r and p0005.cbmej22r encoding almost half a corn phytoene synthase.

SEQ ID NO:4 is the deduced amino acid sequence of almost half a corn phytoene synthase derived from the nucleotide sequence of SEQ ID NO:3.

SEQ ID NO:5 is the nucleotide sequence comprising the contig assembled from a portion of the cDNA insert in clones rds1c.pk005.15, r1r6.pk0028.g3 and rds2c.pk007.f16 encoding the N-terminal 40% of a rice phytoene synthase.

SEQ ID NO:6 is the deduced amino acid sequence of the N-terminal 40% of a rice phytoene synthase derived from the nucleotide sequence of SEQ ID NO:5.

SEQ ID NO:7 is the nucleotide sequence comprising the contig assembled from a portion of the cDNA insert in clones r10n.pk109.j7 and r10n.pk120.p4 encoding a portion of a rice phytoene synthase 2.

SEQ ID NO:8 is the deduced amino acid sequence of a portion of a rice phytoene synthase 2 derived from the nucleotide sequence of SEQ ID NO:7.

SEQ ID NO:9 is the nucleotide sequence comprising the contig assembled from the entire cDNA insert in clone r10.pk0005.e5 and a portion of the cDNA insert in clones rca1n.pk001.18 and rlm1n.pk001.a4 encoding the C-terminal two thirds of a rice phytoene synthase.

SEQ ID NO:10 is the deduced amino acid sequence of the C-terminal two thirds of a rice phytoene synthase derived from the nucleotide sequence of SEQ ID NO:9.

SEQ ID NO:11 is the nucleotide sequence comprising the entire cDNA insert in clone sl1.pk0029.h5 encoding the C-terminal two thirds of a soybean phytoene synthase 2.

SEQ ID NO:12 is the deduced amino acid sequence of the C-terminal two thirds of a soybean phytoene synthase 2 derived from the nucleotide sequence of SEQ ID NO:11.

SEQ ID NO:13 is the nucleotide sequence comprising the entire cDNA insert in clone sl2.pk0045.b10 encoding an entire soybean phytoene synthase.

SEQ ID NO:14 is the deduced amino acid sequence of an entire soybean phytoene synthase derived from the nucleotide sequence of SEQ ID NO:13.

SEQ ID NO:15 is the nucleotide sequence comprising the entire cDNA insert in clone wr1.pk0139.g3 encoding the C-terminal two thirds of a wheat phytoene synthase 2.

SEQ ID NO:16 is the deduced amino acid sequence of the C-terminal two thirds of a wheat phytoene synthase 2 derived from the nucleotide sequence of SEQ ID NO:15.

SEQ ID NO:17 is the nucleotide sequence comprising the contig assembled from the entire cDNA insert in clone cbn2.pk0051.e8 and a portion of the cDNA insert in clones p0031.ccmaj44r and p0097.cqrag63r encoding a portion of a corn zeaxanthin epoxidase.

SEQ ID NO:18 is the deduced amino acid sequence of a portion of a corn zeaxanthin epoxidase derived from the nucleotide sequence of SEQ ID NO:17.

SEQ ID NO:19 is the nucleotide sequence comprising the contig assembled from the entire cDNA insert in clone cr1n.pk0033.d8 and a portion of the cDNA insert in clones p0110.cgsmp01r, p0012.cglae05r and p0088.c1rim55r encoding the C-terminal half of a corn zeazanthin epoxidase.

SEQ ID NO:20 is the deduced amino acid sequence of the C-terminal half of a corn zeazanthin epoxidase derived from the nucleotide sequence of SEQ ID NO:19.

SEQ ID NO:21 is the nucleotide sequence comprising the entire cDNA insert in clone sl1.pk0015.c4 encoding a portion of a soybean zeaxanthin epoxidase.

SEQ ID NO:22 is the deduced amino acid sequence of a portion of a soybean zeaxanthin epoxidase derived from the nucleotide sequence of SEQ ID NO:21.

SEQ ID NO:23 is the nucleotide sequence comprising the 5'-terminal portion of the cDNA insert in clone sl2.pk0109.b6 encoding the N-terminal three quarters of a soybean zeaxanthin epoxidase.

SEQ ID NO:24 is the deduced amino acid sequence of the N-terminal three quarters of a soybean zeaxanthin epoxidase. derived from the nucleotide sequence of SEQ ID NO:23.

SEQ ID NO:25 is the nucleotide sequence comprising the 3'-terminal portion of the cDNA insert in clone sl2.pk0109.b6 encoding the C-terminal fifth of a soybean zeaxanthin epoxidase.

SEQ ID NO:26 is the deduced amino acid sequence of the C-terminal fifth of a soybean zeaxanthin epoxidase derived from the nucleotide sequence of SEQ ID NO:25.

SEQ ID NO:27 is the amino acid sequence of a *Lycopersicon esculentum* phytoene synthase, NCBI gi Accession No. 585747.

SEQ ID NO:28 is the amino acid sequence of a *Cucumis melo* phytoene synthase, NCBI gi Accession No. 1346882.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, the term "isolated polynucleotide refers to a polynucleotide that is substantially free from other nucleic acid sequences, such as other chromosomal and extrachromosomal DNA and TNA that normally accompany or interact with the isolated polynucleotide as found in its naturally occurring environment. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the amino acid sequences was performed using the Clustal method of alignment (Higgins, D. G. and Sharp, P. M. (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the phytoene synthase or the zeaxanthin epoxidase proteins as set forth in SEQ ID NOs:2, 4, 6, 8, 10, 12, 14, 16, 18, 20, 22, 24 and 26. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed MRNA upstream of the translation start sequence. The translation leader sequence may affect processing of the primary transcript to MRNA, MRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting MRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (MRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100: 1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein T. M. et al. (1987) *Nature (London)* 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several carotenoid biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Carotenoid Biosynthetic Enzymes

| Enzyme | Clone | Plant |
|---|---|---|
| Phytoene Synthase | Contig of: p0008.cb3ld95rb csi1.pk0034.d8 | Corn |
| | Contig of: | Corn |

TABLE 1-continued

Carotenoid Biosynthetic Enzymes

| Enzyme | Clone | Plant |
|---|---|---|
| | p0121.cfrmo87r p0091.cmarc67r p0005.cbmej22r | |
| | Contig of: rds1c.pk005.15 rlr6.pk0028.g3 rds2c.pk007.f16 | Rice |
| | Contig of: rl0n.pk109.j7 rl0n.pk120.p4 | Rice |
| | Contig of: rlm1n.pk001.a4 rca1n.pk001.18 rl0.pk0005.e5 | Rice |
| | sl1.pk0029.h5 | Soybean |
| | sl2.pk0045.b10 | Soybean |
| | wr1.pk0139.g3 | Wheat |
| Zeaxanthin Epoxidase | contig of: cbn2.pk0051.e8 p0031.ccmaj44r p0097.cqrag63r | Corn |
| | Contig of: p0110.cgsmp01r p0012.cglae05r p0088.clrim55r cr1n.pk0033.d8 | Corn |
| | sl1.pk0015.c4 | Soybean |
| | sl2.pk0109.b6 | Soybean |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other phytoene synthases or zeaxanthin epoxidases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' CDNA fragments can be isolated (Ohara et al., (1989) *Proc. Natl. Acad. Sci. USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed phytoene synthase or zeaxanthin epoxidase are present at higher or lower levels than normal or in cell types or developmental stages in which they are not normally found. This would have the effect of altering the level of lycopene or zeaxanthin in those cells. Because the nucleotide sequence of corn clone csil.pk0034.d8 is so divergent from known phytoene synthase genes it may be possible to overexpress it in transgenic plants without causing co-supression. Co-suppression of phytoene synthase in rice may re-direct the carbon flux towards tocopherol biosynthesis to improve the grain eating qualities. Manipulation of the levels of zeaxanthin epoxidase in transgenic corn may result in higher levels of zeaxanthin, an important ingredient in animal feed.

Overexpression of the phytoene synthase or the zeaxanthin epoxidase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant carotenoid biosynthetic enzyme to different cellular compartments, or to facilitate its secretion from the cell. It is thus envisioned that the chimeric gene described above may be further supplemented by altering the coding sequence to encode phytoene synthase or zeaxanthin epoxidase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding phytoene synthase or zeaxanthin epoxidase in plants for some applications. In order to accomplish this, a chimeric gene designed for co-suppression of the instant carotenoid biosynthetic enzyme can be constructed by linking a gene or gene fragment encoding a phytoene synthase or a zeaxanthin epoxidase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant phytoene synthase or zeaxanthin epoxidase (or portions thereof) may be produced in heterologous host cells, particularly in the cells of microbial hosts, and can be used to prepare antibodies to the these proteins by methods well known to those skilled in the art. The antibodies are useful for detecting phytoene synthase or zeaxanthin epoxidase in situ in cells or in vitro in cell extracts. Preferred heterologous host cells for production of the instant phytoene synthase or zeaxanthin epoxidase are microbial hosts. Microbial expression systems and expression vectors containing regulatory sequences that direct high level expression of foreign proteins are well known to those skilled in the art. Any of these could be used to construct a chimeric gene for production of the instant phytoene synthase or zeaxanthin epoxidase. This chimeric gene could then be introduced into appropriate microorganisms via transformation to provide high level expression of the encoded carotenoid biosynthetic enzyme. An example of a vector for high level expression of the instant phytoene synthase or zeaxanthin epoxidase in a bacterial host is provided (Example 7).

Additionally, the instant phytoene synthase or zeaxanthin epoxidase can be used as targets to facilitate design and/or identification of inhibitors of those enzymes that may be useful as herbicides. This is desirable because the phytoene synthase or the zeaxanthin epoxidase described herein catalyze various steps in carotenoid biosynthesis. Accordingly, inhibition of the activity of one or more of the enzymes described herein could lead to inhibition plant growth. Thus, the instant phytoene synthase or zeaxanthin epoxidase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the phytoene synthase or the zeaxanthin epoxidase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a phytoene synthase or a zeaxanthin epoxidase can be identified and obtained. This mutant plant can then be used to determine or confirm the natural function of the phytoene synthase or the zeaxanthin epoxidase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cbn2 | Corn Developing Kernel Two Days After Pollination | cbn2.pk0051.e8 |
| cr1n | Corn Root From 7 Day Old Seedlings* | cr1n.pk0033.d8 |
| csi1 | Corn Silk | csi1.pk0034.d8 |
| p0005 | Corn Immature Ear | p0005.cbmej22r |
| p0008 | Corn Leaf, 3-Weeks-Old | p0008.cb3ld95rb |
| p0012 | Corn Middle ¾ of the 3rd Leaf Blade and Mid Rib From Green Leaves Treated with Jasmonic Acid (1 mg/ml in 0.02% Tween 20) for 24 Hours Before Collection | p0012.cglae05r |
| p0031 | Corn Shoot Culture | p0031.ccmaj44r |
| p0088 | Corn Leaf From Mutant Plant** Prior to Genetic Lesion Formation | p0088.clrim55r |
| p0091 | Corn Roots 2 and 3 Days After Germination, Pooled | p0091.cmarc67r |

TABLE 2-continued cDNA Libraries from Corn, Rice, Soybean and Wheat

| Library | Tissue | Clone |
|---------|--------|-------|
| p0097 | Corn V9 Whorl Section (7 cm) From Plant Infected Four Times With European Corn Borer | p0097.cqrag63r |
| p0110 | Corn (Stages V3/V4) Leaf Tissue Minus Midrib Harvested 4 Hours, 24 Hours and 7 Days After Infiltration With Salicylic Acid, Pooled* | p0110.cgsmp01r |
| p0121 | Corn Shank Ear Tissue Collected 5 Days After Pollination* | p0121.cfrmo87r |
| rca1n | Rice Callus* | rca1n.pk001.l8 |
| rds1c | Rice Developing Seeds | rds1c.pk005.l5 |
| rds2c | Rice Developing Seeds From Middle of the Plant | rds2c.pk007.fl6 |
| rl0 | Rice 15 Day Old Leaf | rl0.pk0005.e5 |
| rl0n | Rice 15 Day Old Leaf* | rl0n.pk109.j7<br>rl0n.pk120.p4 |
| rlm1n | Rice Leaf 15 Days After Germination Harvested 2–72 Hours Following Infection With *Magnaporta grisea* (4360-R-62 and 4360-R-67) Normalized at 30 Degrees C. for 24 Hours Using 10 Fold Excess Driver | rlm1n.pk001.a4 |
| rls6 | Rice Leaf 15 Days After Germination, 6 Hours After Infection of Strain *Magaporthe grisea* 4360-R-67 (AVR2-YAMO); Susceptible | rlr6.pk0028.g3 |
| sl1 | Soybean Two-Week-Old Developing Seedlings | sl1.pk0015.c4<br>sl1.pk0029.h5 |
| sl2 | Soybean Two-Week-Old Developing Seedlings Treated With 2.5 ppm chlorimuron | sl2.pk0045.b10<br>sl2.pk0109.b6 |
| wr1 | Wheat Root From 7 Day Old Seedling | wr1.pk0139.g3 |

*These libraries were normalized essentially as described in U.S. Pat. No. 5,482,845
**Simmons, C. et al. (1998) Mol. Plant Microbe Interact. 11:1110–1118 cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) Science 252:1651). The resulting ESTs were analyzed using a Perkin Elmer Model 377 fluorescent sequencer.

Example 2

Identification of cDNA Clones

ESTs encoding carotenoid biosynthetic enzymes were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Phytoene Synthase

The BLASTX search using the EST sequences from clones csi1.pk0034.d8, ssm.pk0011.d9, sl1.pk0069.e4, sl1.pk0029.h5, sl1.pk0073.g10, sl1.pk0031.b8 and wr1.pk0139.g3 revealed similarity of the proteins encoded by the cDNAs to Phytoene Synthase from corn, *Arabidopsis thaliana, Lycopersicon esculentum, Cucumis melo,* and *Capsicum annum* (GenBank Accession Nos. U32636, L25812, L23424, Z37543, X68017 respectively). Further analysis of the sequences from clones ssm.pk0011.d9 and sl1.pk0069.e4 revealed a significant region of overalp, thus affording the assembly of a contig encoding a portion of a soybean Phytoene Synthase. Likewise, further analysis of the sequences from clones sl1.pk0029.h5 and sl1.pk0073.g10 revealed a significant region of overalp, thus affording the assembly of an additional contig encoding a portion of a soybean Phytoene Synthase. The BLAST results for each of these ESTs and contigs are shown in Table 3:

TABLE 3

BLAST Results for Clones Encoding Polypeptides Homologous to Phytoene Synthase

| Clone | Organism | GenBank Accession No. | BLAST pLog Score |
|-------|----------|----------------------|------------------|
| csi1.pk0034.d8 | Maize | U32636 | 33.00 |
| Contig of:<br>ssm.pk0011.d9<br>sl1.pk0069.e4 | *Arabidopsis thaliana* | L25812 | 54.40 |
| Contig of:<br>sl1.pk0029.h5<br>sl1.pk0073.g10 | *Lycopersicon esculentum* | L23424 | 20.00 |
| sl1.pk0031.b8 | *Cucumis melo* | Z37543 | 50.00 |
| wr1.pk0139.g3 | *Capsicum annum* | X68017 | 31.70 |

TBLASTN analysis of the proprietary plant EST database indicated that other corn rice and soybean clones besides those mentioned above encoded phytoene synthetase. The BLASTX search using the nucleotide sequences of the contig assembled from a portion of the cDNA insert in clones p0121.cfrmo87r, p0091.cmarc67r and p0005.cbmej22r revealed similarity of the proteins encoded by the cDNAs to phytoene synthase from *Capsicum annuum* (NCBI gi Accession No. 585749). The BLASTX search using the nucleotide sequences of the contig assembled from a portion of the cDNA insert in clones rds1c.pk005.15, rlr6.pk0028.g3 and rds2c.pk007.f16 and of the contig assembled from the entire cDNA insert in clone rl0.pk0005.e5 and a portion of the cDNA insert in clones rlm1n.pk001.a4 and rca1n.pk001.18 revealed similarity of the proteins encoded by the cDNAs to phytoene synthase from *Zea mays* (NCBI gi Accession No. 1346883). The BLASTX search using the nucleotide sequences from the contig assembled of a portion of the cDNA insert in clones r10n.pk109j7 and r10n.pk120.p4 revealed similarity of the proteins encoded by the cDNAs to phytoene synthase 2 from *Lycopersicon esculentum* (NCBI gi Accession No. 585747). BLASTX search using the nucleotide sequences from the entire cDNA insert in clone sl2.pk0045.b10 revealed similarity of the proteins encoded by the cDNAs to phytoene synthase from *Narcissus pseudonarcissus* (NCBI gi Accession No. 1709885). The BLAST results for each of these sequences are shown in Table 4:

TABLE 4

BLAST Results for Clones Encoding Polypeptides Homologous to Phytoene Synthase

| Clone | Organism | NCBI gi Accession No. | BLAST pLog Score |
|---|---|---|---|
| Contig of: p0121.cfrmo87r p0091.cmarc67r p0005.cbmej22r | *Capsicum annuum* | 585749 | 89.22 |
| Contig of: rds1c.pk005.15 rlr6.pk0028.g3 rds2c.pk007.f16 | *Zea mays* | 1346883 | 54.22 |
| Contig of: r10n.pk109.j7 r10n.pk120.p4 | *Lycopersicon esculentum* | 585747 | 54.30 |
| Contig of: rlm1n.pk001.a4 rca1n.pk001.l8 rl0.pk0005.e5 | *Zea mays* | 1346883 | 132.0 |
| sl2.pk0045.b10 | *Narcissus pseudonarcissus* | 1709885 | 176.0 |

The sequence of the entire cDNA insert in clone csi1.pk0034.d8 was determined and a contig assembled with this sequence and a portion of the cDNA insert from clone p0008.cb31d95rb. The sequence of this contig is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value of 132.0 versus the *Lycopersicon esculentum* phytoene synthase 2 sequence (NCBI gi Accession No. 585747; SEQ ID NO:27). The sequence of the contig assembled of a portion of the cDNA insert from clones p0121.cfrmo87r, p0091.cmarc67r and p0005.cbmej22r is shown in SEQ ID NO:3; the deduced amino acid sequence of this cDNA is shown in SEQ ID NO:4. The sequence of the contig assembled of a portion of the cDNA insert from clones rds1c.pk005.15, rlr6.pk0028.g3 and rds2c.pk007.f16 is shown in SEQ ID NO:5; the deduce amino acid sequence of this cDNA is shown in SEQ ID NO:6. The sequence of the contig asssembled of a portion of the cDNA insert from clones r10n.pk109.j7 and r10n.pk120.p4 is shown in SEQ ID NO:7; the deduced amino acid sequence of this cDNA is shown in SEQ ID NO:8. The sequence of the contig assembled from the entire cDNA insert in clone r10.pk0005.e5 and a portion of the cDNA insert from clones rlm1n.pk001.a4 and rca1n.pk001.18 is shown in SEQ ID NO:9; the deduced amino acid sequence of this cDNA is shown in SEQ ID NO:10. The sequence of the entire cDNA insert in clone sl1.pk0029.h5 was determined and is shown in SEQ ID NO:11; the deduced amino acid sequence of this cDNA is shown in SEQ ID NO:12. The EST sequences from clones ssm.pk001.d9, sl1.pk0069.e4 and sl1.pk0073.g10 are included in the sequence from the entire cDNA insert in clone sl1.pk0029.h5. The amino acid sequence set forth in SEQ ID NO:12 was evaluated by BLASTP, yielding a pLog value of 114.0 versus the *Cucumis melo* sequence (NCBI gi Accession No. 1346882). The sequence of the entire cDNA insert in clone sl2.pk0045.b10 was determined and is shown in SEQ ID NO:13; the deduced amino acid sequence of this cDNA is shown in SEQ ID NO:14. The EST sequences from clone sl1.pk003.b8 is included in the sequence of the entire cDNA insert from clone sl2.pk0045.b10. The amino acid sequence set forth in SEQ ID NO:14 was evaluated by BLASTP, yielding a pLog value of 153.0 versus the *Cucumis melo* sequence. The sequence of the entire cDNA insert in clone wr1.pk0139.g3 was determined and is shown in SEQ ID NO:15; the deduced amino acid sequence of this cDNA is shown in SEQ ID NO:16. The amino acid sequence set forth in SEQ ID NO:16 was evaluated by BLASTP, yielding a pLog value of 118.0 versus the *Lycopersion esculentum* sequence. FIG. 1 presents an alignment of the amino acid sequences set forth in SEQ ID NOs:2 and 14 with the *Lycopersion esculentum* sequence (SEQ ID NO:27) and the *Cucumis melo* sequence (SEQ ID NO:28). The data in Table 5 presents a calculation of the percent similarity of the amino acid sequences set forth in SEQ ID NOs:2 and 14 with the *Lycopersion esculentum* sequence (SEQ ID NO:27) and the *Cucumis melo* sequence (SEQ ID NO:28).

TABLE 5

Percent Similarity of Amino Acid Sequences Deduced From the Nucleotide Sequences of cDNA Clones Encoding Polypeptides Homologous to Phytoene Synthase

| | | Percent Similarity to | |
|---|---|---|---|
| Clone | SEQ ID NO. | 1346882 | 585747 |
| Contig of: p0008.cb3ld95rb csi1.pk0034.d8 | 2 | 57.0 | 78.1 |
| Contig of: p0121.cfrmo87r p0091.cmarc67r p0005.cbmej22r | 4 | 70.4 | 74.2 |
| Contig of: rds1c.pk005.15 rlr6.pk0028.g3 rds2c.pk007.f16 | 6 | 47.6 | 32.3 |
| Contig of: r10n.pk109.j7 r10n.pk120.p4 | 8 | 82.4 | 82.4 |
| Contig of: rlm1n.pk001.a4 rca1n.pk001.l8 rl0.pk0005.e5 | 10 | 77.0 | 77.8 |
| sl1.pk0029.h5 | 12 | 77.1 | 78.7 |
| sl2.pk0045.b10 | 14 | 66.8 | 78.4 |
| wr1.pk0139.g3 | 16 | 78.7 | 81.1 |

Sequence alignments and percent similarity calculations were performed using the Megalign program of the LASARGENE bioinformatics computing suite (DNASTAR Inc., Madison, Wis.). Multiple alignment of the amino acid sequences was performed using the Clustal method of alignment (Higgins, D. G. and Sharp, P. M. (1989) *CABIOS.* 5:151–153) with the default parameters (GAP PENALTY=10, GAP LENGTH PENALTY=10).

Sequence alignments and BLAST scores and probabilities indicate that the instant nucleic acid fragments encode entire or nearly entire corn and soybean phytoene synthase and portions of corn, rice, soybean and wheat phytoene synthase isozymes. These sequences represent the first rice, soybean and wheat sequences encoding phytoene synthase, an entire corn variant which is 55.7% similar to the corn sequences available in the art (NCBI gi Accession Nos. 1346883 and 1098665) and a portion of a corn variant which is 72.0% similar to the art sequences.

Example 4

Characterization of cDNA Clones Encoding Zeaxanthin Epoxidase

The BLASTX search using the nucleotide sequences from clones cbn2.pk0051.e8 and cr1n.pk0033.d8, and the EST sequences from clone sl1.pk0015.c4 revealed similarity of the proteins encoded by the cDNAs to Zeaxanthin Epoxidase from *Lycopersion esculentum* and *Nicotiana plumbaginifolia* (GenBank Accession Nos. Z83835 and X95732, respectively). The BLAST results for each of these sequences are shown in Table 6:

TABLE 6

BLASTn Results for Clones Encoding Polypeptides Homologous to Zeaxanthin Epoxidase

| Clone | Organism | GenBank Accession No. | BLAST pLog Score |
| --- | --- | --- | --- |
| cbn2.pk0051.e8 | *Lycopersicon esculentum* | Z83835 | 45.52 |
| cr1n.pk0033.d8 | *Nicotiana plumbaginifolia* | X95732 | 65.70 |
| sl1.pk0015.c4 | *Lycopersicon esculentum* | Z83835 | 8.30 |

TBLASTN analysis of the proprietary plant EST database indicated that another soybean clone besides sl1.pk0015.c4 also encoded zeaxanthin epoxidase. The BLASTX search using the EST sequences from the 5'terminal and 3'terminal portions of the cDNA insert in clone sl2.pk0109.b6 revealed similarity of the proteins encoded by the cDNAs to zeaxanthin epoxidase from *Prunus armeniaca* (NCBI gi Accession No. 3264757), with pLog values of>254 and 41.70, respectively.

The sequence of the entire cDNA insert in clone cbn2.pk0051.e8 was determined and a contig assembled with this sequence and a portion of the cDNA insert from clones p0031.ccmaj44r and p0097.cqrag63r. The nucleotide sequence of this contig is shown in SEQ ID NO:17; the deduced amino acid sequence of this cDNA is shown in SEQ ID NO:18. The sequence of the entire cDNA insert in clone cr1n.pk0033.d8 was determined and a contig assembled with this sequence and a portion of the cDNA insert from clones p0110.cgsmp01r, p0012.cglae05r and p0088.clrim55r. The nucleotide sequence of this contig is shown in SEQ ID NO:19; the deduced amino acid sequence of this cDNA is shown in SEQ ID NO:20. The sequence of the entire cDNA insert in clone sl1.pk0015.c4 was determined and is shown in SEQ ID NO:21; the deduced amino acid sequence of this cDNA is shown in SEQ ID NO:22. The sequence of the 5'terminus of the cDNA insert in clone sl2.pk109.b6 was determined and is shown in SEQ ID NO:23; the deduced amino acid sequence of this cDNA is shown in SEQ ID NO:24. The sequence of the 3'terminus of the cDNA insert in clone sl2.pk0109.b6 was determined and is shown in SEQ ID NO:25; the deduced amino acid sequence of this cDNA is shown in SEQ ID NO:26.

The data in Table 7 presents a calculation of the percent similarity of the amino acid sequences set forth in SEQ ID NOs: 18, 20, 22, 24 and 26 and the *Lycopersion esculentum* and *Prunus armeniaca* sequences.

TABLE 7

Percent Similarity of Amino Acid Sequences Deduced From the Nucleotide Sequences of cDNA Clones Encoding Polypeptides Homologous to Zeaxanthin Epoxidase

| | | Percent Identity to | |
| --- | --- | --- | --- |
| Clone | SEQ ID NO. | 1772985 | 3264757 |
| Contig of: cbn2.pk0051.e8 p0031.ccmaj44r p0097.cqrag63r | 18 | 55.1 | 56.6 |
| Contig of: p0110.cgsmp01r p0012.cglae05r p0088.clrim55r cr1n.pk0033.d8 | 20 | 66.5 | 64.9 |
| sl1.pk0015.c4 | 22 | 51.9 | 51.9 |
| 5'end of sl2.pk0109.b6 | 24 | 66.1 | 72.7 |
| 3'end of sl2.pk0109.b6 | 26 | | |

Sequence alignments and percent similarity calculations were performed using the Megalign program of the LASARGENE bioinformatics computing suite (DNASTAR Inc., Madison, Wis.). Multiple alignment of the amino acid sequences was performed using the Clustal method of alignment (Higgins, D. G. and Sharp, P. M. (1989) *CABIOS*. 5:151–153) with the default parameters (GAP PENALTY-10, GAP LENGTH PENALTY=10).

Sequence alignments and BLAST scores and probabilities indicate that the instant nucleic acid fragments encode entire or nearly entire soybean zeaxanthin epoxidase and portions of corn and soybean zeaxanthin epoxidase isozymes. These sequences represent the first corn and soybean sequences encoding zeaxanthin epoxidase.

Example 5

Expression of Chimeric Genes in Monocot Cells

A chimeric gene comprising a cDNA encoding a carotenoid biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR. The amplified DNA is then digested with restriction enzymes Nco I and SmaI and fractionated on an agarose gel. The appropriate band can be isolated from the gel and combined with a 4.9 kb Nco I-Sma I fragment of the plasmid pML 103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (SequenaseTm DNA Sequencing Kit; U.S. Biochemical). The resulting plasmid construct would comprise a chimeric gene encoding, in the 5' to 3' direction, the maize 27 kD zein promoter, a cDNA fragment encoding a carotenoid biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein T. M. et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a BiolisticTM PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 6

Expression of Chimeric Genes in Dicot Cells

A seed-specific expression cassette composed of the promoter and transcription terminator from the gene encoding the p subunit of the seed storage protein phaseolin from the bean *Phaseolus vulgaris* (Doyle et al. (1986) *J. Biol. Chem.* 261:9228–9238) can be used for expression of the instant carotenoid biosynthetic enzyme in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding a carotenoid biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein T. M. et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from *Cauliflower Mosaic* Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the carotenoid biosynthetic enzyme and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant carotenoid biosynthetic enzymes can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTGTM low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the carotenoid biosynthetic enzyme are then screened for the correct orientation with respect to the T7 promoter by restriction enzyme analysis.

For high level expression, a plasmid clone with the cDNA insert in the correct orientation relative to the T7 promoter can be transformed into *E coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Carotenoid Biosynthetic Enzymes The carotenoid biosynthetic enzymes described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant carotenoid biosynthetic enzymes may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant carotenoid biosynthetic enzymes, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the carotenoid biosynthetic enzymes are expressed as fusion proteins, the purification protocol may include the use of an affinity resin which is specific for the fusion protein tag attached to the expressed enzyme or an affinity resin containing ligands which are specific for the enzyme. For example, a carotenoid biosynthetic enzyme may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the carotenoid biosynthetic enzymes disclosed herein. Assays may be conducted under well known experimental conditions which permit optimal enzymatic activity. For example, assays for phytoene synthase are presented by Neudert U. et al. (1998) *Biochim. Biophys. Acta* 1392:51–58. Assays for zeaxanthin epoxidase are presented by Bouvier F. et al. (1996) *J. Biol. Chem.* 271:28861–28867).

What is claimed is:

1. An isolated polynucleotide comprising:
   (a) a nucleotide sequence encoding a polypeptide having phytoene synthase activity, wherein the amino acid sequence of the polypeptide and the amino acid sequence of SEQ ID NO:14 have at least 80% sequence identity based on the Clustal alignment method, or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of SEQ ID NO:14 have at least 85% sequence identity based on the Clustal alignment method.

3. The polynucleotide of claim 1, wherein the amino acid sequence of the polypeptide and the amino acid sequence of SEQ ID NO:14 have at least 90% sequence identity based on the Clustal alignment method.

4. The polynucleotide of claim 1, wherein the amino acid sequence of the polypeptide and the amino acid sequence of SEQ ID NO:14 have at least 95% sequence identity based on the Clustal alignment method.

5. The polynucleotide of claim 1 wherein the polypeptide comprises the amino acid sequence of SEQ ID NO:14.

6. The polynucleotide of claim 1, wherein the nucleotide sequence comprises the nucleotide sequence of SEQ ID NO:13.

7. A cell comprising the polynucleotide of claim 1.

8. The cell of claim 7, wherein the cell is selected from the group consisting of a yeast cell, a bacterial cell and a plant cell.

9. A transgenic plant comprising the polynucleotide of claim 1.

10. A method for transforming a cell comprising transforming into a cell the polynucleotide of claim 1.

11. A method for producing a transgenic plant comprising (a) transforming a plant cell with the polynucleotide of claim 1, and (b) regenerating a transgenic plant from the transformed plant cell.

12. A recombinant DNA construct comprising the polynucleotide of claim 1 operably linked to at least one regulatory sequence.

13. A vector comprising the polynucleotide of claim 1.

14. A seed comprising the recombinant DNA construct of claim 12.

* * * * *

SEQUENCE LISTING

<160> NUMBER OF SEQ ID NOS: 28

<210> SEQ ID NO 1
<211> LENGTH: 1448
<212> TYPE: DNA
<213> ORGANISM: Zea mays

<400> SEQUENCE: 1

```
cggaggaaga ggaggaggag agggtcctcg gctggggcct cctcggcgac gcctacgacc    60
gctgcggcga ggtctgcgcc gagtacgcca agaccttta cctcggcacg cagctcatga   120
ctcctgagcg gcgcaaagcc gtctgggcga tctacgtgtg gtgcagaaga actgacgagc   180
tagtggacgg tcccaacgcg tcctacatca cgccgaccgc tctcgaccgc tgggagaagc   240
ggctggagga tctctttgag ggccgcccgt acgacatgta cgacgccgcg ctctcggaca   300
ccgtgtccaa gttccccgtc gatatccagc cgttcaaaga catggtccaa ggaatgaggc   360
tggacctgtg gaagtcgagg tacatgacct tcgacgagct ctacctctac tgctactacg   420
tcgccggcac gcagctcatg actcctgagc ggcgcaaagc cgtctgggcg atctacgtgt   480
ggtgcagaag aactgacgag ctagtggacg gtcccaacgc gtcctacatc acgccgaccg   540
ctctcgaccg ctgggagaag cggctggagg atctctttga gggccgcccg tacgacatgt   600
acgacgccgc gctctcggac actgtgtcca agttccccgt cgatatccag ccgttcaaag   660
acatggtcca aggaatgagg ctggacctgt ggaagtcgag gtacatgacc ttcgacgagc   720
tctacctcta ctgctactac gtcgccggca ccgtcggcct catgacggtg cctgtcatgg   780
gcatcgctcc cgactccaag gcctcgaccg agagcgtgta caatgctgct ctggctctcg   840
gcatcgctaa ccagctgacg aatattctca gagacgtggg cgaagatgcg aggaggggga   900
gaatatacct tccgttggac gagcttgcgc aggcaggtct cacggaagag gacatattca   960
gagggaaagt gaccggcaag tggaggaggt tcatgaaggc ccagatccag cgtgccaggc  1020
tcttctttga tgaggcggag aagggcgtca cccatctcga ctctgctagc agatggccgg  1080
tgctcgcgtc tctgtggctg tacaggcaga tccttgatgc cattgaggca aacgactaca  1140
acaacttcac caagcgtgcg tacgtcggca aggccaagaa gctgctgtcg ttaccgcttg  1200
```

```
catatgcaag ggctgcggtt gcaccatgaa ccatccgtag atcacatctt tttttctttt   1260
tcttttccaa acccaccttg ttttgcccca cccttccttt tttttttgta tataatcagc   1320
ttcagctgcc tgcatggcat aagccttgcc tgttcagggt gattccatgt ccctaaatac   1380
tcaatcagct cttgttacaa ggaatggaga attagaattc gagaagcgta aaaaaaaaa    1440 aaaaaaaa                                                            1448
```

<210> SEQ ID NO 2
<211> LENGTH: 408
<212> TYPE: PRT
<213> ORGANISM: Zea mays

<400> SEQUENCE: 2

```
Glu Glu Glu Glu Glu Arg Val Leu Gly Trp Gly Leu Leu Gly Asp
 1               5                   10                  15

Ala Tyr Asp Arg Cys Gly Glu Val Cys Ala Glu Tyr Ala Lys Thr Phe
            20                  25                  30

Tyr Leu Gly Thr Gln Leu Met Thr Pro Glu Arg Arg Lys Ala Val Trp
        35                  40                  45

Ala Ile Tyr Val Trp Cys Arg Arg Thr Asp Glu Leu Val Asp Gly Pro
    50                  55                  60

Asn Ala Ser Tyr Ile Thr Pro Thr Ala Leu Asp Arg Trp Glu Lys Arg
65                  70                  75                  80

Leu Glu Asp Leu Phe Glu Gly Arg Pro Tyr Asp Met Tyr Asp Ala Ala
                85                  90                  95

Leu Ser Asp Thr Val Ser Lys Phe Pro Val Asp Ile Gln Pro Phe Lys
            100                 105                 110

Asp Met Val Gln Gly Met Arg Leu Asp Leu Trp Lys Ser Arg Tyr Met
        115                 120                 125

Thr Phe Asp Glu Leu Tyr Leu Tyr Cys Tyr Tyr Val Ala Gly Thr Gln
    130                 135                 140

Leu Met Thr Pro Glu Arg Arg Lys Ala Val Trp Ala Ile Tyr Val Trp
145                 150                 155                 160

Cys Arg Arg Thr Asp Glu Leu Val Asp Gly Pro Asn Ala Ser Tyr Ile
                165                 170                 175

Thr Pro Thr Ala Leu Asp Arg Trp Glu Lys Arg Leu Glu Asp Leu Phe
            180                 185                 190

Glu Gly Arg Pro Tyr Asp Met Tyr Asp Ala Ala Leu Ser Asp Thr Val
        195                 200                 205

Ser Lys Phe Pro Val Asp Ile Gln Pro Phe Lys Asp Met Val Gln Gly
    210                 215                 220

Met Arg Leu Asp Leu Trp Lys Ser Arg Tyr Met Thr Phe Asp Glu Leu
225                 230                 235                 240

Tyr Leu Tyr Cys Tyr Tyr Val Ala Gly Thr Val Gly Leu Met Thr Val
                245                 250                 255

Pro Val Met Gly Ile Ala Pro Asp Ser Lys Ala Ser Thr Glu Ser Val
            260                 265                 270

Tyr Asn Ala Ala Leu Ala Leu Gly Ile Ala Asn Gln Leu Thr Asn Ile
        275                 280                 285

Leu Arg Asp Val Gly Glu Asp Ala Arg Arg Gly Arg Ile Tyr Leu Pro
    290                 295                 300

Leu Asp Glu Leu Ala Gln Ala Gly Leu Thr Glu Glu Asp Ile Phe Arg
305                 310                 315                 320

Gly Lys Val Thr Gly Lys Trp Arg Arg Phe Met Lys Gly Gln Ile Gln
```

```
                         325                 330                 335
Arg Ala Arg Leu Phe Phe Asp Glu Ala Glu Lys Gly Val Thr His Leu
                340                 345                 350
Asp Ser Ala Ser Arg Trp Pro Val Leu Ala Ser Leu Trp Leu Tyr Arg
            355                 360                 365
Gln Ile Leu Asp Ala Ile Glu Ala Asn Asp Tyr Asn Asn Phe Thr Lys
        370                 375                 380
Arg Ala Tyr Val Gly Lys Ala Lys Lys Leu Leu Ser Leu Pro Leu Ala
385                 390                 395                 400
Tyr Ala Arg Ala Ala Val Ala Pro
                405

<210> SEQ ID NO 3
<211> LENGTH: 888
<212> TYPE: DNA
<213> ORGANISM: Zea mays
<220> FEATURE:
<221> NAME/KEY: unsure
<222> LOCATION: (5)
<221> NAME/KEY: unsure
<222> LOCATION: (10)
<221> NAME/KEY: unsure
<222> LOCATION: (18)
<221> NAME/KEY: unsure
<222> LOCATION: (225)
<221> NAME/KEY: unsure
<222> LOCATION: (725)
<221> NAME/KEY: unsure
<222> LOCATION: (809)
<221> NAME/KEY: unsure
<222> LOCATION: (836)
<221> NAME/KEY: unsure
<222> LOCATION: (862)

<400> SEQUENCE: 3
ggaangggtn gatacagntt gtatggcttg acggttgacg ataatgacgc tctgagaata    60
ccagagcgga tttaagtttc taaactaacg ctaggacggt gaaagtggta gatacagttt   120
gtatggcttg acggttgacg ataatgacga gggaagggat gacactgatt gatcgctgac   180
gtgggtgttc tatctccgcg cacgcgcgct cctgttcagt gtggngcagg agaacggacg   240
agctcgtgga cggccccaac gcgtcccaca tctcggcgct ggcgctggac cggtgggagt   300
cgcggctgga ggacatcttc gccggccggc cgtacgacat gctcgacgcc gccctgtccg   360
acaccgtcgc caggttcccc gtcgacatcc agccgttcag ggacatgatc gagggatgc    420 gcatggacct gaagaagtcc cggtacagga gcttcgacga gctgtacctc tactgctact   480
acgtggccgg caccgtgggg ctgatgagcg tcccggtgat gggcatctcg ccggcgtcca   540
gggcggccac cgagacggtg tacaagggg cgctggcgct gggcctggcg aaccagctca   600
ccaacatcct cagggacgtc ggcgaggacg ccaggagggg acggatctac ctcccgcaag   660
acgagctgga gatggcgggg ctctccgacg ccgaacgtcc tggacgggcc gcgtcaacga   720
acgantggaa gggcttcatg aagggccaga ttcgcgaagg ccaaaacctt cttcaaggca   780
agccggaagg aaagcgccaa cgaagctcna accaaggaga gccgattgcc ggtgtngtct   840
tctctgctcc ttgtaccggc anatcctcga acgaaatcga aggccaac                888

<210> SEQ ID NO 4
<211> LENGTH: 186
<212> TYPE: PRT
<213> ORGANISM: Zea mays
<220> FEATURE:
<221> NAME/KEY: UNSURE
```

```
<222> LOCATION: (3)
<221> NAME/KEY: UNSURE
<222> LOCATION: (169)

<400> SEQUENCE: 4
```

Val Trp Xaa Arg Arg Thr Asp Glu Leu Val Asp Gly Pro Asn Ala Ser
 1               5                  10                  15

His Ile Ser Ala Leu Ala Leu Asp Arg Trp Glu Ser Arg Leu Glu Asp
            20                  25                  30

Ile Phe Ala Gly Arg Pro Tyr Asp Met Leu Asp Ala Ala Leu Ser Asp
        35                  40                  45

Thr Val Ala Arg Phe Pro Val Asp Ile Gln Pro Phe Arg Asp Met Ile
    50                  55                  60

Glu Gly Met Arg Met Asp Leu Lys Lys Ser Arg Tyr Arg Ser Phe Asp
65                  70                  75                  80

Glu Leu Tyr Leu Tyr Cys Tyr Tyr Val Ala Gly Thr Val Gly Leu Met
                85                  90                  95

Ser Val Pro Val Met Gly Ile Ser Pro Ala Ser Arg Ala Ala Thr Glu
            100                 105                 110

Thr Val Tyr Lys Gly Ala Leu Ala Leu Gly Leu Ala Asn Gln Leu Thr
        115                 120                 125

Asn Ile Leu Arg Asp Val Gly Glu Asp Ala Arg Arg Gly Arg Ile Tyr
130                 135                 140

Leu Pro Gln Asp Glu Leu Glu Met Ala Gly Leu Ser Asp Ala Glu Arg
145                 150                 155                 160

Pro Gly Arg Ala Ala Ser Thr Asn Xaa Trp Lys Gly Phe Met Lys Gly
                165                 170                 175

Gln Ile Arg Glu Gly Gln Asn Leu Leu Gln
            180                 185

```
<210> SEQ ID NO 5
<211> LENGTH: 766
<212> TYPE: DNA
<213> ORGANISM: Oryza sativa
<220> FEATURE:
<221> NAME/KEY: unsure
<222> LOCATION: (658)

<400> SEQUENCE: 5
```

| | | | | |
|---|---|---|---|---|
| cgcagactct cgactttgtc actagcatca ttgcttgatg atcgatgctg agctgcaacc | 60 |
| aagcaccagc atatccttc cttcattcct tcctggtgct ggtagaagaa gaacaagcta | 120 |
| gctagagtga taagagctag ctaccttgca gatcgatctc cggccagcga ttgatcccat | 180 |
| ccagtataat aatggcggcc atcacgctcc tacgttcagc gtctcttccg ggcctctccg | 240 |
| acgccctcgc ccgggacgct gctgccgtcc aacatgtctg ctcctcctac ctgcccaaca | 300 |
| acaaggagaa gaagagggag gtggatcctc tgctcgctca agtacgcctg ccttggcgtc | 360 |
| gaccctgccc cgggcgagat tgcccggacc tcgccggtgt actccagcct caccgtcacc | 420 |
| cctgctggag aggccgtcat ctcctcggag cagaaggtgt acgacgtcgt cctcaagcag | 480 |
| gcagcattgc tcaaacgcca cctgcgccca caaccacaca ccattcccat cgttcccaag | 540 |
| gacctggacc tgccaagaaa cggcctcaag caggcctatc atcgctgcgg agagatctgc | 600 |
| gaggagtatg ccaagacctt ttaccttgga actatgctca tgacggagga ccgacggngc | 660 |
| gccatatggg ccatctatgt gtggtgtagg agggcaaatg agcttgtaga tggaccaaat | 720 |
| gcctcgcaca tcacaacgtc aagcctggac ggtggggaaa agaggt | 766 |

```
<210> SEQ ID NO 6
<211> LENGTH: 164
<212> TYPE: PRT
<213> ORGANISM: Oryza sativa
<220> FEATURE:
<221> NAME/KEY: UNSURE
<222> LOCATION: (129)

<400> SEQUENCE: 6

Met Ser Ala Pro Pro Thr Cys Pro Thr Thr Arg Arg Arg Gly Arg
  1               5                  10                  15

Trp Ile Leu Cys Ser Leu Lys Tyr Ala Cys Leu Gly Val Asp Pro Ala
                 20                  25                  30

Pro Gly Glu Ile Ala Arg Thr Ser Pro Val Tyr Ser Ser Leu Thr Val
             35                  40                  45

Thr Pro Ala Gly Glu Ala Val Ile Ser Ser Glu Gln Lys Val Tyr Asp
         50                  55                  60

Val Val Leu Lys Gln Ala Ala Leu Leu Lys Arg His Leu Arg Pro Gln
 65                  70                  75                  80

Pro His Thr Ile Pro Ile Val Pro Lys Asp Leu Asp Leu Pro Arg Asn
                 85                  90                  95

Gly Leu Lys Gln Ala Tyr His Arg Cys Gly Glu Ile Cys Glu Glu Tyr
            100                 105                 110

Ala Lys Thr Phe Tyr Leu Gly Thr Met Leu Met Thr Glu Asp Arg Arg
        115                 120                 125

Xaa Ala Ile Trp Ala Ile Tyr Val Trp Cys Arg Arg Ala Asn Glu Leu
    130                 135                 140

Val Asp Gly Pro Asn Ala Ser His Ile Thr Thr Ser Ser Leu Asp Gly
145                 150                 155                 160

Gly Glu Lys Arg

<210> SEQ ID NO 7
<211> LENGTH: 476
<212> TYPE: DNA
<213> ORGANISM: Oryza sativa
<220> FEATURE:
<221> NAME/KEY: unsure
<222> LOCATION: (2)
<221> NAME/KEY: unsure
<222> LOCATION: (275)
<221> NAME/KEY: unsure
<222> LOCATION: (453)
<221> NAME/KEY: unsure
<222> LOCATION: (459)

<400> SEQUENCE: 7
cttacatgta agctcgtgcc gaattcngca cgagcttaca ccctaactct tcttacatta      60
caccaaaggc acttgatcga tgggagaaga gattagaaga tctcttcgaa ggcaggccat    120
atgatatgta tgatgcagcc ctctcggaca cagtgtcaaa gtttccagta gatatccagc    180
cattcaaaga catgattgaa ggaatgaggc ttgacctgtg gaaatcaagg tataggagct    240
ttgatgagct ctacctctac tgctactacg ttgctggcac ggttggtctc atgacagtac    300
cggtgatggg gattgccccc gactcgaagg cctcaacccg agagcgtgta caacgctgcg    360 ctagctncttt gggatcgcca acccagctga cgaaatattc tcaagangac gttaggccaa    420
agaacccaag ggagggggaa agaatctaac ccntccaant ggggatgaaa ttggga         476

<210> SEQ ID NO 8
<211> LENGTH: 108
```

<212> TYPE: PRT
<213> ORGANISM: Oryza sativa

<400> SEQUENCE: 8

Pro Asn Ser Ser Tyr Ile Thr Pro Lys Ala Leu Asp Arg Trp Glu Lys
 1               5                  10                  15

Arg Leu Glu Asp Leu Phe Glu Gly Arg Pro Tyr Asp Met Tyr Asp Ala
             20                  25                  30

Ala Leu Ser Asp Thr Val Ser Lys Phe Pro Val Asp Ile Gln Pro Phe
         35                  40                  45

Lys Asp Met Ile Glu Gly Met Arg Leu Asp Leu Trp Lys Ser Arg Tyr
 50                  55                  60

Arg Ser Phe Asp Glu Leu Tyr Leu Tyr Cys Tyr Tyr Val Ala Gly Thr
 65                  70                  75                  80

Val Gly Leu Met Thr Val Pro Val Met Gly Ile Ala Pro Asp Ser Lys
                 85                  90                  95

Ala Gln Pro Glu Ser Val Tyr Asn Ala Ala Leu Ala
             100                 105

<210> SEQ ID NO 9
<211> LENGTH: 1060
<212> TYPE: DNA
<213> ORGANISM: Oryza sativa
<220> FEATURE:
<221> NAME/KEY: unsure
<222> LOCATION: (2)
<221> NAME/KEY: unsure
<222> LOCATION: (275)

<400> SEQUENCE: 9
gnacatcaca ccgtcagccc tgggaccggt gggagaagag gcttgatgat ctcttcaccg      60 gacgcccta cgacatgctt gatgctgcac tttctgatac catctccaag tttcctatag     120
atattcagcc tttcagggac atgatagaag ggatgcggtc agacctcaga aagactagat     180
acaagaactt cgacgagctc tacatgtact gctactatgt tgctggaact gtggggctaa     240
tgagtgttcc tgtgatgggt attgcacccg agtcnaaggc aacaactgaa agtgtgtaca     300
gtgctgcttt ggctctcggg aatgcaaacc agctcacaaa tatactccgt gacgttggag     360
aggacgcgag aagagggagg atatatttac cacaagatga acttgcagag gcaaggctct     420
ctgatgagga catcttcaat ggcgttgtga ctaacaaatg gagaagcttc atgaagagac     480
agatcaagag agctaggatg ttttttgagg aggcagagag aggggtgacc gagctcagcc     540
aggcaagccg gtggccggtc tgggcgtctc tgttgttata ccggcaaatc cttgacgaga     600
tagaagcaaa cgattacaac aacttcacaa agagggcgta cgttgggaag gcgaagaaat     660
tgctagcgct tccagttgca tatggtagat cattgctgat gccctactca ctgagaaata     720
gccagaagta ggaggcggga agaggagata aaggaagat gatgagcagg ttaggcttag     780
ataggaaaaa tcagacagca tctgccttcc gattaatgtt gaggaaatta tattattgtg     840
tgtatcatac atagcatgta tagggaaaat gctgcaggca ggcaggcagg ctaggtgatg     900
gttgaatatt tccttcacat catgtatgta tatccttcct tgatgctaca gcacatatgt     960
atgtatgact ctgaagaaag agcaacctgt atagtagcta accggctatg gcctatgtat    1020
gggccgcaga ggtgagcaaa caaaaaaaaa aaaaaaaaa                           1060

<210> SEQ ID NO 10
<211> LENGTH: 242
<212> TYPE: PRT

<213> ORGANISM: Oryza sativa

<400> SEQUENCE: 10

```
Thr Ser His Arg Gln Pro Trp Asp Arg Trp Glu Lys Arg Leu Asp Asp
  1               5                  10                  15
Leu Phe Thr Gly Arg Pro Tyr Asp Met Leu Asp Ala Ala Leu Ser Asp
             20                  25                  30
Thr Ile Ser Lys Phe Pro Ile Asp Ile Gln Pro Phe Arg Asp Met Ile
         35                  40                  45
Glu Gly Met Arg Ser Asp Leu Arg Lys Thr Arg Tyr Lys Asn Phe Asp
 50                  55                  60
Glu Leu Tyr Met Tyr Cys Tyr Tyr Val Ala Gly Thr Val Gly Leu Met
 65                  70                  75                  80
Ser Val Pro Val Met Gly Ile Ala Pro Glu Ser Lys Ala Thr Thr Glu
                 85                  90                  95
Ser Val Tyr Ser Ala Ala Leu Ala Leu Gly Asn Ala Asn Gln Leu Thr
            100                 105                 110
Asn Ile Leu Arg Asp Val Gly Glu Asp Ala Arg Arg Gly Arg Ile Tyr
        115                 120                 125
Leu Pro Gln Asp Glu Leu Ala Glu Ala Arg Leu Ser Asp Glu Asp Ile
130                 135                 140
Phe Asn Gly Val Val Thr Asn Lys Trp Arg Ser Phe Met Lys Arg Gln
145                 150                 155                 160
Ile Lys Arg Ala Arg Met Phe Phe Glu Glu Ala Glu Arg Gly Val Thr
                165                 170                 175
Glu Leu Ser Gln Ala Ser Arg Trp Pro Val Trp Ala Ser Leu Leu Leu
            180                 185                 190
Tyr Arg Gln Ile Leu Asp Glu Ile Glu Ala Asn Asp Tyr Asn Asn Phe
        195                 200                 205
Thr Lys Arg Ala Tyr Val Gly Lys Ala Lys Lys Leu Leu Ala Leu Pro
    210                 215                 220
Val Ala Tyr Gly Arg Ser Leu Leu Met Pro Tyr Ser Leu Arg Asn Ser
225                 230                 235                 240
Gln Lys
```

<210> SEQ ID NO 11
<211> LENGTH: 992
<212> TYPE: DNA
<213> ORGANISM: Glycine max
<220> FEATURE:
<221> NAME/KEY: unsure
<222> LOCATION: (14)
<221> NAME/KEY: unsure
<222> LOCATION: (23)

<400> SEQUENCE: 11

```
catttctatc gtgnatatgg ctnacatcga cctcaacgac cactttgcct aggtgggaat      60
caaaattgga agaactttc caaggtcgtc catttgatat gcttgatgct gctttatcag     120
atacagttgc caaattccct gttgatatcc agccatttaa agatatgata gaaggaatga     180
gactggatct taagaagcca agatacagaa actttgatga actatatctt tactgttact     240
atgttgctgg gacagttggt ataatgagtg ttccaatcat gggcatttca ccaaattccc     300
aagccacaac agagagtgta tacaatgctg ccttggccct aggcattgca aatcagctaa     360
ccaacatact cagagatgtt ggagaggatg ccagcagagg aagagtgtat cttccacaag     420
atgagttggc tcaagcaggg ctttccgatg aagacatttt tgctggtaag gtgacagaca     480
```

```
agtggaggaa cttcatgaag agccaaatta aaagggcaag aatgttttt gatgaggcag      540 aaaagggagt gacggagctt aatgaagcta gcagatggcc tgtatgggcg tctttgctat      600
tgtatcgcca aatattggac gagatagaag ctaatgatta caacaatttc actagaaggg      660
cttatgtgag caaagccaag aagttacttt ctttgccagc tgcatatgct agatctatgg      720
ttcctccatc aaaaaagtta tcttctgtaa tgaagcata aatcgagcac ttatggcat        780 tctgtagaaa aatggataag gaggaccaca gaaaatggaa aggcacaatt tgtatatgat      840
aaaacaaggc atgatattag tcaatattgg attttgatat tcatatttcc ccgtattttt      900
ttacataaaa aaagtttgga ctaatatttt gttactttag agttaatttt gatgcgagtt      960
atgaattatt tgaactgaaa aaaaaaaaaa aa                                    992
```

<210> SEQ ID NO 12
<211> LENGTH: 252
<212> TYPE: PRT
<213> ORGANISM: Glycine max
<220> FEATURE:
<221> NAME/KEY: UNSURE
<222> LOCATION: (4)

<400> SEQUENCE: 12

```
Phe Leu Ser Xaa Ile Trp Leu Thr Ser Thr Ser Thr Thr Thr Leu Pro
 1               5                  10                  15

Arg Trp Glu Ser Lys Leu Glu Glu Leu Phe Gln Gly Arg Pro Phe Asp
            20                  25                  30

Met Leu Asp Ala Ala Leu Ser Asp Thr Val Ala Lys Phe Pro Val Asp
        35                  40                  45

Ile Gln Pro Phe Lys Asp Met Ile Glu Gly Met Arg Leu Asp Leu Lys
    50                  55                  60

Lys Pro Arg Tyr Arg Asn Phe Asp Glu Leu Tyr Leu Tyr Cys Tyr Tyr
65                  70                  75                  80

Val Ala Gly Thr Val Gly Ile Met Ser Val Pro Ile Met Gly Ile Ser
                85                  90                  95

Pro Asn Ser Gln Ala Thr Thr Glu Ser Val Tyr Asn Ala Ala Leu Ala
            100                 105                 110

Leu Gly Ile Ala Asn Gln Leu Thr Asn Ile Leu Arg Asp Val Gly Glu
        115                 120                 125

Asp Ala Ser Arg Gly Arg Val Tyr Leu Pro Gln Asp Glu Leu Ala Gln
    130                 135                 140

Ala Gly Leu Ser Asp Glu Asp Ile Phe Ala Gly Lys Val Thr Asp Lys
145                 150                 155                 160

Trp Arg Asn Phe Met Lys Ser Gln Ile Lys Arg Ala Arg Met Phe Phe
                165                 170                 175

Asp Glu Ala Glu Lys Gly Val Thr Glu Leu Asn Glu Ala Ser Arg Trp
            180                 185                 190

Pro Val Trp Ala Ser Leu Leu Leu Tyr Arg Gln Ile Leu Asp Glu Ile
        195                 200                 205

Glu Ala Asn Asp Tyr Asn Asn Phe Thr Arg Arg Ala Tyr Val Ser Lys
    210                 215                 220

Ala Lys Lys Leu Leu Ser Leu Pro Ala Ala Tyr Ala Arg Ser Met Val
225                 230                 235                 240

Pro Pro Ser Lys Lys Leu Ser Ser Val Met Lys Thr
                245                 250
```

<210> SEQ ID NO 13
<211> LENGTH: 1397
<212> TYPE: DNA
<213> ORGANISM: Glycine max

<400> SEQUENCE: 13

```
gttttgctaa cacaagtata cactcattct caaaaggttt tcatccaatt tctttccctc      60
tcttttcatt ggtgtgcact ttcacttgtg gagctgcatc aactgcagtg gaaattgtgc     120
tttgttcttg agatgtctgg tgttcttctt tgggtgagtt gtggacccaa agagaacatc     180
aactccttgg tgagtttttc atgcaggagt agtagtggtg gtgaaagaac acaaagaga     240
ttttctggaa tcagttttgc tagtggtact tctgcttttt caagtgcagt ggcagctact     300
gagacttcaa gatcttcaga ggagagggtc tatgaagtgg ttctgaagca agcagctttg     360
gtaaaagaac acaaagggg tacaaaaata gctttggatt tggacaaaga tgttgaggct     420
gatttcaaca atgtggatct gttgaatgcg gcttatgatc ggtgtggtga agtttgtgct     480
gagtatgcca agacatttta cttaggcaca caattgatga ctgcagagcg ccgaaaagca     540
atttgggcaa tttatgtgtg gtgcagaaga actgatgagc tagtggatgg cccaaatgct     600
tcacacatca ccctggggc cttggacagg tgggagcaac gattgagtga tgtttttgaa     660
ggtcgaccct atgatatgta tgatgctgcc ctctcacata ctgtctcaaa gtacccggtt     720
gatattcagc ccttcaagga catgatcgaa gggatgaggg tggacctgag aaagtcaaga     780
tacaataact tgatgagct ctaccttac tgctactatg ttgctgggac agtaggcctt     840
atgagtgtcc cagtaatggg gatagcacca gaatcaaatg cttcatcaga gagcatttat     900
aatgctgcat tggctctagg cattgcaaat caacttacca acatacttag agatgttgga     960
gaagatgcta aagaggaag agtatatctc ccacaagatg aattggcaca agctggcctt    1020
tcagatgatg acatttccg cggaagagtt acagacaaat ggcggaaatt catgaaggga    1080
caaataaaga gggcgaggat gttttttgat gaggcagaga gaggggttgc agagctcaac    1140
tcagctagca ggtggcctgt gtgggcatca ttgttgttgt ataggcaaat attagattcc    1200
attgaagcca atgattataa taacttcaca aaaagggcat atgtaggaaa agtaaagaaa    1260
ctcttgtcac tacctactgc ctatggtttt tcacttctag gccctcagaa gtttaccaaa    1320
atggttagga ggtaactgtt atacaatgtg tgatactttt gagttacaac tgtatacatc    1380
tcaagttaaa aaaaaaa                                                   1397
```

<210> SEQ ID NO 14
<211> LENGTH: 400
<212> TYPE: PRT
<213> ORGANISM: Glycine max

<400> SEQUENCE: 14

```
Met Ser Gly Val Leu Leu Trp Val Ser Cys Gly Pro Lys Glu Asn Ile
  1               5                  10                  15

Asn Ser Leu Val Ser Phe Ser Cys Arg Ser Ser Gly Gly Glu Arg
                 20                  25                  30

Thr Gln Lys Arg Phe Ser Gly Ile Ser Phe Ala Ser Gly Thr Ser Ala
             35                  40                  45

Phe Ser Ser Ala Val Ala Ala Thr Glu Thr Ser Arg Ser Ser Glu Glu
         50                  55                  60

Arg Val Tyr Glu Val Val Leu Lys Gln Ala Ala Leu Val Lys Glu His
 65                  70                  75                  80

Lys Arg Gly Thr Lys Ile Ala Leu Asp Leu Asp Lys Asp Val Glu Ala
```

```
                    85                  90                  95
Asp Phe Asn Asn Val Asp Leu Leu Asn Ala Ala Tyr Asp Arg Cys Gly
                100                 105                 110

Glu Val Cys Ala Glu Tyr Ala Lys Thr Phe Tyr Leu Gly Thr Gln Leu
            115                 120                 125

Met Thr Ala Glu Arg Arg Lys Ala Ile Trp Ala Ile Tyr Val Trp Cys
        130                 135                 140

Arg Arg Thr Asp Glu Leu Val Asp Gly Pro Asn Ala Ser His Ile Thr
145                 150                 155                 160

Pro Gly Ala Leu Asp Arg Trp Glu Gln Arg Leu Ser Asp Val Phe Glu
                165                 170                 175

Gly Arg Pro Tyr Asp Met Tyr Asp Ala Ala Leu Ser His Thr Val Ser
            180                 185                 190

Lys Tyr Pro Val Asp Ile Gln Pro Phe Lys Asp Met Ile Glu Gly Met
        195                 200                 205

Arg Val Asp Leu Arg Lys Ser Arg Tyr Asn Asn Phe Asp Glu Leu Tyr
210                 215                 220

Leu Tyr Cys Tyr Tyr Val Ala Gly Thr Val Gly Leu Met Ser Val Pro
225                 230                 235                 240

Val Met Gly Ile Ala Pro Glu Ser Asn Ala Ser Ser Glu Ser Ile Tyr
                245                 250                 255

Asn Ala Ala Leu Ala Leu Gly Ile Ala Asn Gln Leu Thr Asn Ile Leu
            260                 265                 270

Arg Asp Val Gly Glu Asp Ala Arg Arg Gly Arg Val Tyr Leu Pro Gln
        275                 280                 285

Asp Glu Leu Ala Gln Ala Gly Leu Ser Asp Asp Ile Phe Arg Gly
290                 295                 300

Arg Val Thr Asp Lys Trp Arg Lys Phe Met Lys Gly Gln Ile Lys Arg
305                 310                 315                 320

Ala Arg Met Phe Phe Asp Glu Ala Glu Arg Gly Val Ala Glu Leu Asn
                325                 330                 335

Ser Ala Ser Arg Trp Pro Val Trp Ala Ser Leu Leu Leu Tyr Arg Gln
            340                 345                 350

Ile Leu Asp Ser Ile Glu Ala Asn Asp Tyr Asn Asn Phe Thr Lys Arg
        355                 360                 365

Ala Tyr Val Gly Lys Val Lys Lys Leu Leu Ser Leu Pro Thr Ala Tyr
370                 375                 380

Gly Phe Ser Leu Leu Gly Pro Gln Lys Phe Thr Lys Met Val Arg Arg
385                 390                 395                 400

<210> SEQ ID NO 15
<211> LENGTH: 1021
<212> TYPE: DNA
<213> ORGANISM: Triticum aestivum

<400> SEQUENCE: 15
cggacgagga gaactgatga gctagtggat ggccctaact catcttacat cacgcccaag      60
gcgctcgatc ggtgggagaa gagattagag gatctcttcg aaggccgccc atatgatatg     120
tatgatgcag ccctctcaga tacagcgtca aagtttccaa ttgatatcca gccattcaga     180
gacatgattg aagggatgag gctcgacctt tggaaatcga ggtataggac ctttgacgag     240
ctctacctct actgctacta cgtcgctggc actgtcggtc tcatgacggt accggtgatg     300
gggattgctc cggactcaaa ggcctcagca gagagcgtgt acaatgccgc actggccctt     360
```

-continued

```
ggcattgcca accagctcac aaacatcctc cgagacgtag gagaagactc aagaagggg      420 agaatatacc ttccactgga cgaactggca caggcgggtc tgacagaaga ggacatattc      480
agagggaaag tgacggataa atggaggagg ttcatgaagg gcaaatcca gcgcgccagg      540 ctcttctttg acgaggccga gaaggcgtc atgcatctag actccgcgag cagatggccg      600
gtcctggcat cgctgtggct gtacaggcag atcctggacg ccatcgaggc caacgactac      660
aacaacttca ccaagcgcgc gtacgtgggc aaggcaaaga gttcctgtc tctaccggcc      720 gcgtacgcga gggcggctct ctcgccatga gcaaagcaat cccgtagatc agatgttttt      780
tcttcttctt tttctttctt tttgtcctgt caccctacaa tgattttgt tggctgttgt      840 atatactcag ctatatgttt gccatacgcc cgccgcggta tttaggtcaa gggaccgacg      900
tcgggccccg ctgtactgaa gtctgaaaca cttgttgtta ccacacagtg gagaatcaaa      960
attgctccag ttgaatgaag aagaaacaaa cactcttct tcctaaaaaa aaaaaaaaa      1020 a                                                                      1021
```

<210> SEQ ID NO 16
<211> LENGTH: 248
<212> TYPE: PRT
<213> ORGANISM: Triticum aestivum

<400> SEQUENCE: 16

```
Thr Arg Arg Thr Asp Glu Leu Val Asp Gly Pro Asn Ser Ser Tyr Ile
 1               5                  10                  15

Thr Pro Lys Ala Leu Asp Arg Trp Glu Lys Arg Leu Glu Asp Leu Phe
            20                  25                  30

Glu Gly Arg Pro Tyr Asp Met Tyr Asp Ala Ala Leu Ser Asp Thr Ala
        35                  40                  45

Ser Lys Phe Pro Ile Asp Ile Gln Pro Phe Arg Asp Met Ile Glu Gly
    50                  55                  60

Met Arg Leu Asp Leu Trp Lys Ser Arg Tyr Arg Thr Phe Asp Glu Leu
65                  70                  75                  80

Tyr Leu Tyr Cys Tyr Tyr Val Ala Gly Thr Val Gly Leu Met Thr Val
                85                  90                  95

Pro Val Met Gly Ile Ala Pro Asp Ser Lys Ala Ser Ala Glu Ser Val
            100                 105                 110

Tyr Asn Ala Ala Leu Ala Leu Gly Ile Ala Asn Gln Leu Thr Asn Ile
        115                 120                 125

Leu Arg Asp Val Gly Glu Asp Ser Arg Arg Gly Arg Ile Tyr Leu Pro
    130                 135                 140

Leu Asp Glu Leu Ala Gln Ala Gly Leu Thr Glu Glu Asp Ile Phe Arg
145                 150                 155                 160

Gly Lys Val Thr Asp Lys Trp Arg Arg Phe Met Lys Gly Gln Ile Gln
                165                 170                 175

Arg Ala Arg Leu Phe Phe Asp Glu Ala Glu Lys Gly Val Met His Leu
            180                 185                 190

Asp Ser Ala Ser Arg Trp Pro Val Leu Ala Ser Leu Trp Leu Tyr Arg
        195                 200                 205

Gln Ile Leu Asp Ala Ile Glu Ala Asn Asp Tyr Asn Asn Phe Thr Lys
    210                 215                 220

Arg Ala Tyr Val Gly Lys Ala Lys Lys Phe Leu Ser Leu Pro Ala Ala
225                 230                 235                 240

Tyr Ala Arg Ala Ala Leu Ser Pro
                245
```

<210> SEQ ID NO 17
<211> LENGTH: 722
<212> TYPE: DNA
<213> ORGANISM: Zea mays
<220> FEATURE:
<221> NAME/KEY: unsure
<222> LOCATION: (324)
<221> NAME/KEY: unsure
<222> LOCATION: (525)
<221> NAME/KEY: unsure
<222> LOCATION: (532)
<221> NAME/KEY: unsure
<222> LOCATION: (534)
<221> NAME/KEY: unsure
<222> LOCATION: (539)
<221> NAME/KEY: unsure
<222> LOCATION: (554)
<221> NAME/KEY: unsure
<222> LOCATION: (585)
<221> NAME/KEY: unsure
<222> LOCATION: (613)
<221> NAME/KEY: unsure
<222> LOCATION: (635)
<221> NAME/KEY: unsure
<222> LOCATION: (642)
<221> NAME/KEY: unsure
<222> LOCATION: (645)
<221> NAME/KEY: unsure
<222> LOCATION: (651)
<221> NAME/KEY: unsure
<222> LOCATION: (669)
<221> NAME/KEY: unsure
<222> LOCATION: (675)..(676)
<221> NAME/KEY: unsure
<222> LOCATION: (719)

<400> SEQUENCE: 17

```
gccgtcgacg ccgccgcggc cgacgaggtc atggacgccg gctgcgtcac gggggaccgc        60
gtcaacggca tcgttgacgg cgtttctggc tcctggtaca tcaagtttga tacgtttact       120
cctgcagctg agcgggggct cccggtcaca agggtcatta gccgcatgac gctgcaacag       180
atccttgctc gagcagttgg cgatgacgct atattgaatg gaagccatgt agtcgatttt       240
acagatgatg gcagtaaggt tactgccata ttggaggacg gtaggatatt tgaaggtgac       300
cttttggttg gtgccgatgg aatntggtca aaggtgagga agacactatt cgggcactca       360
gatgccacct attcaggtta catctgcaat tccagtgtag cagattttgt gccacctgat       420
atcgatacag ttgggtaccg agtatttctt ggccacaaac agtacttcgt ctcttcggat       480
gtcggtgctg gtaaaatgca atggtacgct tttcacaatg aagangctgg tngnactgnc       540
cctgaaatgg caanaaagaa aaaattgctt gagatattcg acggntgggt ggataatgtt       600
aatgatttga tanatgcaac tgaggaagaa gcagntcttc gncgngatat ntacggcggc       660
ccacctaanc gatgnnattg gggggaaagg ccgggcacct tgcttgggga tctggccang       720
ct                                                                    722
```

<210> SEQ ID NO 18
<211> LENGTH: 121
<212> TYPE: PRT
<213> ORGANISM: Zea mays
<220> FEATURE:
<221> NAME/KEY: UNSURE
<222> LOCATION: (95)

<400> SEQUENCE: 18

```
Gly Cys Val Thr Gly Asp Arg Val Asn Gly Ile Val Asp Gly Val Ser
  1               5                  10                  15
```

```
Gly Ser Trp Tyr Ile Lys Phe Asp Thr Phe Thr Pro Ala Ala Glu Arg
            20                  25                  30
Gly Leu Pro Val Thr Arg Val Ile Ser Arg Met Thr Leu Gln Gln Ile
        35                  40                  45
Leu Ala Arg Ala Val Gly Asp Asp Ala Ile Leu Asn Gly Ser His Val
    50                  55                  60
Val Asp Phe Thr Asp Asp Gly Ser Lys Val Thr Ala Ile Leu Glu Asp
65                  70                  75                  80
Gly Arg Ile Phe Glu Gly Asp Leu Leu Val Gly Ala Asp Gly Xaa Trp
                85                  90                  95
Ser Lys Val Arg Lys Thr Leu Phe Gly His Ser Asp Ala Thr Tyr Ser
            100                 105                 110
Gly Tyr Ile Cys Asn Ser Ser Val Ala
            115                 120
```

<210> SEQ ID NO 19
<211> LENGTH: 1246
<212> TYPE: DNA
<213> ORGANISM: Zea mays
<220> FEATURE:
<221> NAME/KEY: unsure
<222> LOCATION: (367)

<400> SEQUENCE: 19

```
aagaaagagg agctcggaca angcagagcg ccatcgttcg gtttccttgc tgaattcccg      60
atcgctcgct cgctcgaaaa gaaagaagct agcttttagc atggctattg aggatggtta    120
ccagctggct gtagagctag agaatgcctg caagagagt gtcaaaactg aaactcctat     180
agacatagtt tcctccttga ggcgctacga gaaagagaga aggctgcgtg ttgctattat    240
acatggactg gcaagaatgg cagcaatcat ggctaccacc tatagaccgt acttgggtgt    300
tggtctaggg cctttatcgt ttttgaccaa gttgcggata ccacaccctg aagagtcgg    360
tggcagnttc ttcatcaagt atggaatgcc tacgatgttg agctgggtgc ttggtggcaa    420
cagctcaaaa ctagaaggaa gacttttaag ctgccgactt tctgacaagg caaatgacca    480
gctttatcaa tggtttgagg atgatgacgc actggaagaa gctatgggtg agaatggta    540
cctcatcgca acaagtgaag gaaactgcaa tagcttgcag cccattcatt taattaggga    600
tgagcagagg tcactctttg ttggaagccg tcagatcct aatgattcag cttcttccct     660
atcattgtcc tctccacaga tatcagaaag acatgctact atcacatgca agaataaagc    720
tttctatctg actgatctcg gaagcgaaca tggtacctgg attaccgaca atgaaggtag    780
acgttaccgc gtgccaccaa acttccagt tcgtttccat ccctccgatg tcattgagtt     840
tggttccgat aagaaggcta tgttccgggt gaaggtgctg aacacgctcc cgtatgaatc    900
tgcaagaagt gggaatcggc agcaacagca agtccttcag gcagcatgaa tggagacact    960
ggctaccacc actatcatca gccacactgt actgtacagc atccggtaaa gacacaacac   1020
tgcatcacga aaggataca ctcgttctcg aatatttgtc gtctgctagt tcaattttaa    1080
actaaaacgt gacaaatgaa aaacgaagg aagtagaaga tatgtcaaaa cacatgcaat    1140
ttttgcatcc atgaagatgc caaacaggat cttgaatact agcacctagc ggattgaaat   1200
aatgaagttg cagttctgcg tgaactggat tgtacgatag ggatag                  1246
```

<210> SEQ ID NO 20
<211> LENGTH: 315
<212> TYPE: PRT

```
<213> ORGANISM: Zea mays
<220> FEATURE:
<221> NAME/KEY: UNSURE
<222> LOCATION: (7)
<221> NAME/KEY: UNSURE
<222> LOCATION: (122)

<400> SEQUENCE: 20
```

Arg Lys Arg Ser Ser Asp Xaa Ala Glu Arg His Arg Ser Val Ser Leu
 1               5                  10                  15

Leu Asn Ser Arg Ser Leu Ala Arg Ser Lys Arg Lys Leu Ala Phe
            20                  25                  30

Ser Met Ala Ile Glu Asp Gly Tyr Gln Leu Ala Val Glu Leu Glu Asn
        35                  40                  45

Ala Trp Gln Glu Ser Val Lys Thr Glu Thr Pro Ile Asp Ile Val Ser
    50                  55                  60

Ser Leu Arg Arg Tyr Glu Lys Glu Arg Leu Arg Val Ala Ile Ile
65                  70                  75                  80

His Gly Leu Ala Arg Met Ala Ala Ile Met Ala Thr Thr Tyr Arg Pro
                85                  90                  95

Tyr Leu Gly Val Gly Leu Gly Pro Leu Ser Phe Leu Thr Lys Leu Arg
            100                 105                 110

Ile Pro His Pro Gly Arg Val Gly Gly Xaa Phe Phe Ile Lys Tyr Gly
        115                 120                 125

Met Pro Thr Met Leu Ser Trp Val Leu Gly Gly Asn Ser Ser Lys Leu
    130                 135                 140

Glu Gly Arg Leu Leu Ser Cys Arg Leu Ser Asp Lys Ala Asn Asp Gln
145                 150                 155                 160

Leu Tyr Gln Trp Phe Glu Asp Asp Ala Leu Glu Glu Ala Met Gly
                165                 170                 175

Gly Glu Trp Tyr Leu Ile Ala Thr Ser Glu Gly Asn Cys Asn Ser Leu
            180                 185                 190

Gln Pro Ile His Leu Ile Arg Asp Glu Gln Arg Ser Leu Phe Val Gly
        195                 200                 205

Ser Arg Ser Asp Pro Asn Asp Ser Ala Ser Ser Leu Ser Leu Ser Ser
    210                 215                 220

Pro Gln Ile Ser Glu Arg His Ala Thr Ile Thr Cys Lys Asn Lys Ala
225                 230                 235                 240

Phe Tyr Leu Thr Asp Leu Gly Ser Glu His Gly Thr Trp Ile Thr Asp
                245                 250                 255

Asn Glu Gly Arg Arg Tyr Arg Val Pro Pro Asn Phe Pro Val Arg Phe
            260                 265                 270

His Pro Ser Asp Val Ile Glu Phe Gly Ser Asp Lys Lys Ala Met Phe
        275                 280                 285

Arg Val Lys Val Leu Asn Thr Leu Pro Tyr Glu Ser Ala Arg Ser Gly
    290                 295                 300

Asn Arg Gln Gln Gln Gln Val Leu Gln Ala Ala
305                 310                 315

```
<210> SEQ ID NO 21
<211> LENGTH: 926
<212> TYPE: DNA
<213> ORGANISM: Glycine max

<400> SEQUENCE: 21
```
gcacgagcat gatggtgata ttttaatagg agcagatgga atatggtcag aagtgcgttc    60

-continued

```
aaaactctttt gggcagcaag aagcaaatta ctcgggtttc acatgctaca gtggattaac    120
aagctatgtg cccccatata ttgataccgt tgggtatcgg tgttcttgg gcttgaacca     180 gtactttgtt gcttcagatg ttggccatgg aagatgcag tggtatgctt ccatgggga      240 accccttca agtgacccct tcccagaagg taagaagaag aggcttttgg atctctttgg     300
taattggtgc gatgaagtga ttgcactcat atcagaaaca ccagaacata tgattataca    360
gagggatata tatgacagag acatgatcaa cacttgggga attgggagag tgactttgtt    420
aggtgatgca gcacatccaa tgcaaccaaa tcttggtcaa ggagggtgta tggcaataga    480
ggattgttac caactgatac ttgagctaga caaggttgct aaacatggct ctgacgggtc    540
tgaagttatc tcagctctta aagatatga aagaaaaga atcccccgag ttagggtgtt     600
acacacagct agcaggatgg catcgcaaat gttagtcaac taccggcctt atattgaatt    660
taaattttgg cctctatcaa atgtaacaac tatgcagata aagcaccctg gcattcatgt    720
agctcaagcc cttttcaagt tcactttcc acaatttgtt acttggatga ttgctggcca    780
tgggttgtgg tgaacactca tgcaacttga aaataaaaag ggctcaacaa ttttaacatg    840
atggtagtta aaagttaatt ttattgggct atgtaggaac ttttctttcg gaataaacgt    900
gccataattt aaaaaaaaaa aaaaaa                                          926
```

<210> SEQ ID NO 22
<211> LENGTH: 263
<212> TYPE: PRT
<213> ORGANISM: Glycine max

<400> SEQUENCE: 22

```
His Glu His Asp Gly Asp Ile Leu Ile Gly Ala Asp Gly Ile Trp Ser
  1               5                  10                  15

Glu Val Arg Ser Lys Leu Phe Gly Gln Gln Glu Ala Asn Tyr Ser Gly
                 20                  25                  30

Phe Thr Cys Tyr Ser Gly Leu Thr Ser Tyr Val Pro Pro Tyr Ile Asp
             35                  40                  45

Thr Val Gly Tyr Arg Val Phe Leu Gly Leu Asn Gln Tyr Phe Val Ala
         50                  55                  60

Ser Asp Val Gly His Gly Lys Met Gln Trp Tyr Ala Phe His Gly Glu
 65                  70                  75                  80

Pro Pro Ser Ser Asp Pro Phe Pro Glu Gly Lys Lys Arg Leu Leu
                 85                  90                  95

Asp Leu Phe Gly Asn Trp Cys Asp Glu Val Ile Ala Leu Ile Ser Glu
                100                 105                 110

Thr Pro Glu His Met Ile Ile Gln Arg Asp Ile Tyr Asp Arg Asp Met
            115                 120                 125

Ile Asn Thr Trp Gly Ile Gly Arg Val Thr Leu Leu Gly Asp Ala Ala
        130                 135                 140

His Pro Met Gln Pro Asn Leu Gly Gln Gly Gly Cys Met Ala Ile Glu
145                 150                 155                 160

Asp Cys Tyr Gln Leu Ile Leu Glu Leu Asp Lys Val Ala Lys His Gly
                165                 170                 175

Ser Asp Gly Ser Glu Val Ile Ser Ala Leu Arg Arg Tyr Glu Lys Lys
            180                 185                 190

Arg Ile Pro Arg Val Arg Val Leu His Thr Ala Ser Arg Met Ala Ser
        195                 200                 205

Gln Met Leu Val Asn Tyr Arg Pro Tyr Ile Glu Phe Lys Phe Trp Pro
    210                 215                 220
```

-continued

Leu Ser Asn Val Thr Thr Met Gln Ile Lys His Pro Gly Ile His Val
225                 230                 235                 240

Ala Gln Ala Leu Phe Lys Phe Thr Phe Pro Gln Phe Val Thr Trp Met
            245                 250                 255

Ile Ala Gly His Gly Leu Trp
            260

<210> SEQ ID NO 23
<211> LENGTH: 1528
<212> TYPE: DNA
<213> ORGANISM: Glycine max

<400> SEQUENCE: 23

```
cacaaaacac acacacacat attctcacac aaactgcaac catggctact accttatgtt      60
acaattctct taacccttca acaccgtttt tctcaagaac ccatttctca gttcccttga     120
ataaagagct tccactggat gcttcacctt ttgttgttgg ctataactgt ggtgtaggat     180
gcagaacaag gaagcaaagg aagaaagtga tgcatgtgaa gtgtgcagtg gtggaggctc     240
caccaggtgt ttcaccctca gcaaaagatg ggaatgggaa ccacccctcc cgaagaagca     300
gcttcgtata cttgtggctg gtggagggat tggagggttg gttttgtgctt tgggctgcaa     360
agagaaaggg gtttgaggtg atggtgtttg agaaggactt gagtgctata agaggggagg     420
gacagtatag gggtccaatt cagattcaga gcaatgcttt ggctgctttg gaagctattg     480
attcagaggt tgctgatgaa gttatgagag ttggttgcat cactggtgat agaatcaatg     540
gacttgtaga tggggtttct ggttcttggt acgtcaagtt tgatacattc actcctgcag     600
tggaacgtgg gcttcctgtc acaagagtta ttagtcgaat ggttttacaa agatccttg     660
ctcgcgcagt tggggaagat atcattatga atgccagtaa tgttgttaat tttgtggatg     720
atggaaacaa ggtaacagta gagctagaga atggtcagaa atatgaagga gatgtcttgg     780
ttggagcgga tggaatatgg tccaaggtga ggaagcagtt atttgggctc acagaagctg     840
tttactctgg ttatacttgt tatactggca ttgcagattt tgtgcctgct gacattgaaa     900
ctgttggata ccgagtattc ttgggacaca acaatactt tgtatcttca gatgttggtg     960
cgggaaagat gcaatggtat gcatttcaca aagaaactcc cggtgggggtt gatgagccca    1020
acggaaaaaa ggaaaggttg cttaggatat ttgagggctg gtgtgaaagt gctgtagatc    1080
tgatacttgc cacagaagaa gaagcaattc taagacgaga catatatgac aggataccaa    1140
cattgacatg gggaaagggt cgcgtgactt tgcttggtga ttccgtccat gccatgcagc    1200
caaatatggg ccaaggaggg tgcatggcta ttgaggacag ttatcaactt gcatgggagt    1260
tggagaatgc atgggaacaa agtattaaat cagggagtcc aattgacatt gattcttccc    1320
taaggagcta cgagagagaa agaagactac gagttgccat tattcatgga atggctagaa    1380
tggcggctct catggcttcc acttacaagg catatctggg tgttggtctt ggcccttag    1440
aattttttgac taagtttcgt ataccacatc ctggaagagt tggaggaagg tttttttgttg    1500
acatcatgat gccttctatg ttgatgtt                                        1528
```

<210> SEQ ID NO 24
<211> LENGTH: 495
<212> TYPE: PRT
<213> ORGANISM: Glycine max

<400> SEQUENCE: 24

Met Ala Thr Thr Leu Cys Tyr Asn Ser Leu Asn Pro Ser Thr Thr Val

-continued

```
  1                   5                   10                  15
Phe Ser Arg Thr His Phe Ser Val Pro Leu Asn Lys Glu Leu Pro Leu
                20                  25                  30

Asp Ala Ser Pro Phe Val Val Gly Tyr Asn Cys Gly Val Gly Cys Arg
            35                  40                  45

Thr Arg Lys Gln Arg Lys Lys Val Met His Val Lys Cys Ala Val Val
        50                  55                  60

Glu Ala Pro Pro Gly Val Ser Pro Ser Ala Lys Asp Gly Asn Gly Asn
65                      70                  75                  80

His Pro Phe Arg Arg Ser Ser Phe Val Tyr Leu Trp Leu Val Glu Gly
                    85                  90                  95

Leu Glu Gly Trp Phe Leu Leu Trp Ala Ala Lys Arg Lys Gly Phe Glu
                100                 105                 110

Val Met Val Phe Glu Lys Asp Leu Ser Ala Ile Arg Gly Glu Gly Gln
            115                 120                 125

Tyr Arg Gly Pro Ile Gln Ile Gln Ser Asn Ala Leu Ala Ala Leu Glu
        130                 135                 140

Ala Ile Asp Ser Glu Val Ala Asp Glu Val Met Arg Val Gly Cys Ile
145                 150                 155                 160

Thr Gly Asp Arg Ile Asn Gly Leu Val Asp Gly Val Ser Gly Ser Trp
                165                 170                 175

Tyr Val Lys Phe Asp Thr Phe Thr Pro Ala Val Glu Arg Gly Leu Pro
                180                 185                 190

Val Thr Arg Val Ile Ser Arg Met Val Leu Gln Glu Ile Leu Ala Arg
            195                 200                 205

Ala Val Gly Glu Asp Ile Ile Met Asn Ala Ser Asn Val Val Asn Phe
210                 215                 220

Val Asp Asp Gly Asn Lys Val Thr Val Glu Leu Glu Asn Gly Gln Lys
225                 230                 235                 240

Tyr Glu Gly Asp Val Leu Val Gly Ala Asp Gly Ile Trp Ser Lys Val
                245                 250                 255

Arg Lys Gln Leu Phe Gly Leu Thr Glu Ala Val Tyr Ser Gly Tyr Thr
            260                 265                 270

Cys Tyr Thr Gly Ile Ala Asp Phe Val Pro Ala Asp Ile Glu Thr Val
        275                 280                 285

Gly Tyr Arg Val Phe Leu Gly His Lys Gln Tyr Phe Val Ser Ser Asp
    290                 295                 300

Val Gly Ala Gly Lys Met Gln Trp Tyr Ala Phe His Lys Glu Thr Pro
305                 310                 315                 320

Gly Gly Val Asp Glu Pro Asn Gly Lys Lys Glu Arg Leu Leu Arg Ile
                325                 330                 335

Phe Glu Gly Trp Cys Glu Ser Ala Val Asp Leu Ile Leu Ala Thr Glu
            340                 345                 350

Glu Glu Ala Ile Leu Arg Arg Asp Ile Tyr Asp Arg Ile Pro Thr Leu
        355                 360                 365

Thr Trp Gly Lys Gly Arg Val Thr Leu Leu Gly Asp Ser Val His Ala
    370                 375                 380

Met Gln Pro Asn Met Gly Gln Gly Gly Cys Met Ala Ile Glu Asp Ser
385                 390                 395                 400

Tyr Gln Leu Ala Trp Glu Leu Glu Asn Ala Trp Glu Gln Ser Ile Lys
                405                 410                 415

Ser Gly Ser Pro Ile Asp Ile Asp Ser Ser Leu Arg Ser Tyr Glu Arg
            420                 425                 430
```

Glu Arg Arg Leu Arg Val Ala Ile Ile His Gly Met Ala Arg Met Ala
        435                 440                 445

Ala Leu Met Ala Ser Thr Tyr Lys Ala Tyr Leu Gly Val Gly Leu Gly
    450                 455                 460

Pro Leu Glu Phe Leu Thr Lys Phe Arg Ile Pro His Pro Gly Arg Val
465                 470                 475                 480

Gly Gly Arg Phe Phe Val Asp Ile Met Met Pro Ser Met Leu Met
                485                 490                 495

<210> SEQ ID NO 25
<211> LENGTH: 686
<212> TYPE: DNA
<213> ORGANISM: Glycine max

<400> SEQUENCE: 25
aacaagatgg aacaggtctt tcaaagccta tatctttaag tcgaaatgag atgaaaccct    60
tcataatcgg gagtgcacca atgcaagata attcaggcag ttcagttaca atttcttcac   120
cacaggtttc tccaacgcat gctcgaatta actataagga tggtgccttc ttcttgattg   180
atttacggag tgagcatggc acctggatca ttgacaacga aggaaagcag taccgggtac   240
ctcctaatta tcctgctcgc atccgtccat ctgatgttat tcagtttggt tctgagaagg   300
tttcgttccg tgttaaggtg acaagctctg ttccaagagt ctcagaaaat gaaagcacac   360
tagcttttgca gggagtatga ctgattctgc tcaattgcaa tttgtaagtt atggaaaaat   420
tatacagcac aaatttgcta ttgtatagta ctatctgcat tgttttaggg tggggtatta   480
taccacagtc tagtcattta agatctgata tgttacatgc ctatatggac atttaagagg   540
gactcttggg tataaatttg ttactccact ccaatacttt ttgtgtatga catttgtaat   600
ttgttagagt tagatttata acatgacaca cataaacttg cacgtgatta aaaaaaaaa    660
aaaaaaaaaa aaaaaaaaa aaaaaa                                         686

<210> SEQ ID NO 26
<211> LENGTH: 125
<212> TYPE: PRT
<213> ORGANISM: Glycine max

<400> SEQUENCE: 26

Gln Asp Gly Thr Gly Leu Ser Lys Pro Ile Ser Leu Ser Arg Asn Glu
1               5                   10                  15

Met Lys Pro Phe Ile Ile Gly Ser Ala Pro Met Gln Asp Asn Ser Gly
            20                  25                  30

Ser Ser Val Thr Ile Ser Ser Pro Gln Val Ser Pro Thr His Ala Arg
        35                  40                  45

Ile Asn Tyr Lys Asp Gly Ala Phe Phe Leu Ile Asp Leu Arg Ser Glu
    50                  55                  60

His Gly Thr Trp Ile Ile Asp Asn Glu Gly Lys Gln Tyr Arg Val Pro
65                  70                  75                  80

Pro Asn Tyr Pro Ala Arg Ile Arg Pro Ser Asp Val Ile Gln Phe Gly
                85                  90                  95

Ser Glu Lys Val Ser Phe Arg Val Lys Val Thr Ser Ser Val Pro Arg
            100                 105                 110

Val Ser Glu Asn Glu Ser Thr Leu Ala Leu Gln Gly Val
        115                 120                 125

<210> SEQ ID NO 27

```
<211> LENGTH: 310
<212> TYPE: PRT
<213> ORGANISM: Lycopersicon esculentum

<400> SEQUENCE: 27

Asp Pro Asp Ile Val Leu Pro Gly Asn Leu Gly Leu Ser Glu Ala
 1               5                  10                  15

Tyr Asp Arg Cys Gly Glu Val Cys Ala Glu Tyr Ala Lys Thr Phe Tyr
            20                  25                  30

Leu Gly Thr Met Leu Met Thr Pro Asp Arg Arg Arg Ala Ile Trp Ala
        35                  40                  45

Ile Tyr Val Trp Cys Arg Arg Thr Asp Glu Leu Val Asp Gly Pro Asn
    50                  55                  60

Ala Ser His Ile Thr Pro Gln Ala Leu Asp Arg Trp Glu Ala Arg Leu
65                  70                  75                  80

Glu Asp Ile Phe Asn Gly Arg Pro Phe Asp Met Leu Asp Ala Ala Leu
                85                  90                  95

Ser Asp Thr Val Ser Arg Phe Pro Val Asp Ile Gln Pro Phe Arg Asp
            100                 105                 110

Met Val Glu Gly Met Arg Met Asp Leu Trp Lys Ser Arg Tyr Asn Asn
        115                 120                 125

Phe Asp Glu Leu Tyr Leu Tyr Cys Tyr Tyr Val Ala Gly Thr Val Gly
    130                 135                 140

Leu Met Ser Val Pro Ile Met Gly Ile Ala Pro Glu Ser Lys Ala Thr
145                 150                 155                 160

Thr Glu Ser Val Tyr Asn Ala Ala Leu Ala Leu Gly Ile Ala Asn Gln
                165                 170                 175

Leu Thr Asn Ile Leu Arg Asp Val Gly Glu Asp Ala Arg Arg Gly Arg
            180                 185                 190

Val Tyr Leu Pro Gln Asp Glu Leu Ala Gln Ala Gly Leu Ser Asp Glu
        195                 200                 205

Asp Ile Phe Ala Gly Lys Val Thr Asp Lys Trp Arg Ile Phe Met Lys
    210                 215                 220

Lys Gln Ile Gln Arg Ala Arg Lys Phe Phe Asp Glu Ala Glu Lys Gly
225                 230                 235                 240

Val Thr Glu Leu Ser Ser Ala Ser Arg Trp Pro Val Leu Ala Ser Leu
                245                 250                 255

Leu Leu Tyr Arg Lys Ile Leu Asp Glu Ile Glu Ala Asn Asp Tyr Asn
            260                 265                 270

Asn Phe Thr Arg Arg Ala Tyr Val Ser Lys Pro Lys Lys Leu Leu Thr
        275                 280                 285

Leu Pro Ile Ala Tyr Ala Arg Ser Leu Val Pro Pro Lys Ser Thr Ser
    290                 295                 300

Cys Pro Leu Ala Lys Thr
305                 310

<210> SEQ ID NO 28
<211> LENGTH: 410
<212> TYPE: PRT
<213> ORGANISM: Zea mays

<400> SEQUENCE: 28

Met Ala Ile Ile Leu Val Arg Ala Ala Ser Pro Gly Leu Ser Ala Ala
 1               5                  10                  15

Asp Ser Ile Ser His Gln Gly Thr Leu Gln Cys Ser Thr Leu Leu Lys
            20                  25                  30
```

-continued

```
Thr Lys Arg Pro Ala Ala Arg Arg Trp Met Pro Cys Ser Leu Leu Gly
         35                  40                  45

Leu His Pro Trp Glu Ala Gly Arg Pro Ser Pro Ala Val Tyr Ser Ser
         50                  55                  60

Leu Pro Val Asn Pro Ala Gly Glu Ala Val Val Ser Ser Glu Gln Lys
 65                  70                  75                  80

Val Tyr Asp Val Val Leu Lys Gln Ala Ala Leu Leu Lys Arg Gln Leu
                 85                  90                  95

Arg Thr Pro Val Leu Asp Ala Arg Pro Gln Asp Met Asp Met Pro Arg
                100                 105                 110

Asn Gly Leu Lys Glu Ala Tyr Asp Arg Cys Gly Glu Ile Cys Glu Glu
            115                 120                 125

Tyr Ala Lys Thr Phe Tyr Leu Gly Thr Met Leu Met Thr Glu Glu Arg
130                 135                 140

Arg Arg Ala Ile Trp Ala Ile Tyr Val Trp Cys Arg Arg Thr Asp Glu
145                 150                 155                 160

Leu Val Asp Gly Pro Asn Ala Asn Tyr Ile Thr Pro Thr Ala Leu Asp
                165                 170                 175

Arg Trp Glu Lys Arg Leu Glu Asp Leu Phe Thr Gly Arg Pro Tyr Asp
                180                 185                 190

Met Leu Asp Ala Ala Leu Ser Asp Thr Ile Ser Arg Phe Pro Ile Asp
            195                 200                 205

Ile Gln Pro Phe Arg Asp Met Ile Glu Gly Met Arg Ser Asp Leu Arg
            210                 215                 220

Lys Thr Arg Tyr Asn Asn Phe Asp Glu Leu Tyr Met Tyr Cys Tyr Tyr
225                 230                 235                 240

Val Ala Gly Thr Val Gly Leu Met Ser Val Pro Val Met Gly Ile Ala
                245                 250                 255

Thr Glu Ser Lys Ala Thr Thr Glu Ser Val Tyr Ser Ala Ala Leu Ala
                260                 265                 270

Leu Gly Ile Ala Asn Gln Leu Thr Asn Ile Leu Arg Asp Val Gly Glu
            275                 280                 285

Asp Ala Arg Arg Gly Arg Ile Tyr Leu Pro Gln Asp Glu Leu Ala Gln
            290                 295                 300

Ala Gly Leu Ser Asp Glu Asp Ile Phe Lys Gly Val Val Thr Asn Arg
305                 310                 315                 320

Trp Arg Asn Phe Met Lys Arg Gln Ile Lys Arg Ala Arg Met Phe Phe
                325                 330                 335

Glu Glu Ala Glu Arg Gly Val Asn Glu Leu Ser Gln Ala Ser Arg Trp
            340                 345                 350

Pro Val Trp Ala Ser Leu Leu Leu Tyr Arg Gln Ile Leu Asp Glu Ile
            355                 360                 365

Glu Ala Asn Asp Tyr Asn Asn Phe Thr Lys Arg Ala Tyr Val Gly Lys
370                 375                 380

Gly Lys Lys Leu Leu Ala Leu Pro Val Ala Tyr Gly Lys Ser Leu Leu
385                 390                 395                 400

Leu Pro Cys Ser Leu Arg Asn Gly Gln Thr
                405                 410
```